(12) United States Patent
Lorenzo et al.

(10) Patent No.: US 10,905,430 B2
(45) Date of Patent: Feb. 2, 2021

(54) ANEURYSM DEVICE AND DELIVERY SYSTEM

(71) Applicant: DePuy Synthes Products, Inc., Raynham, MA (US)

(72) Inventors: Juan Lorenzo, Raynham, MA (US); Lacey Gorochow, Raynham, MA (US); Ariel Sotodelvalle, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 237 days.

(21) Appl. No.: 15/879,196

(22) Filed: Jan. 24, 2018

(65) Prior Publication Data
US 2019/0223878 A1 Jul. 25, 2019

(51) Int. Cl.
  *A61B 17/12* (2006.01)
  *A61B 17/00* (2006.01)
  *A61F 2/06* (2013.01)

(52) U.S. Cl.
  CPC .. *A61B 17/12113* (2013.01); *A61B 17/12031* (2013.01); *A61B 17/12172* (2013.01);
  (Continued)

(58) Field of Classification Search
  CPC ........ A61B 17/12031; A61B 17/12113; A61B 17/12118; A61B 17/1214;
  (Continued)

(56) References Cited

U.S. PATENT DOCUMENTS 2,849,002 A  8/1958 Oddo
3,480,017 A  11/1969 Shute
(Continued)

FOREIGN PATENT DOCUMENTS

CA  2395796 A1  7/2001
CA  2 431 594 A1  9/2002
(Continued)

OTHER PUBLICATIONS

Extended European Search Report dated Jun. 5, 2019 in corresponding European Application No. 19153590.5.
(Continued)

*Primary Examiner* — Robert A Lynch
(74) *Attorney, Agent, or Firm* — Troutman Pepper Hamilton Sanders LLP

(57) ABSTRACT

A braid for treating an aneurysm can include a first radially expandable segment operable to move from a collapsed state within a microcatheter to a deployed state distal of the microcatheter. The first radially expandable segment can be capable of radially expanding to form an outer occlusive sack in the aneurysm in the deployed state. The braid can also include a second radially expandable segment operable to move from the collapsed state within the microcatheter to the deployed state distal of the microcatheter, wherein the second radially expandable segment is capable of radially expanding inside the outer occlusive sack to form an inner occlusive sack in the outer occlusive sack in the deployed state. An expansion mechanism can be included and be disposed at a proximal end of the first and second radially expandable segments.

18 Claims, 9 Drawing Sheets

(52) U.S. Cl.
CPC ............... *A61B 2017/00292* (2013.01); *A61B 2017/00345* (2013.01); *A61B 2017/00867* (2013.01); *A61B 2017/1205* (2013.01); *A61B 2017/12054* (2013.01); *A61F 2002/068* (2013.01)

(58) Field of Classification Search
CPC ........ A61B 17/12145; A61B 17/12168; A61B 17/12172; A61B 2017/00292; A61B 2017/00345; A61B 2017/00867; A61B 2017/1205; A61B 2017/12054
See application file for complete search history.

(56) References Cited

U.S. PATENT DOCUMENTS

| | | |
|---|---|---|
| 4,085,757 A | 4/1978 | Pevsner |
| 4,282,875 A | 4/1981 | Serbinenko et al. |
| 4,364,392 A | 12/1982 | Strother et al. |
| 4,395,806 A | 8/1983 | Wonder et al. |
| 4,517,979 A | 5/1985 | Pecenka |
| 4,545,367 A | 10/1985 | Tucci |
| 4,836,204 A | 6/1989 | Landymore et al. |
| 4,991,602 A | 2/1991 | Amplatz et al. |
| 5,002,556 A | 3/1991 | Ishida et al. |
| 5,025,060 A | 6/1991 | Yabuta et al. |
| 5,065,772 A | 11/1991 | Cox, Jr. |
| 5,067,489 A | 11/1991 | Lind |
| 5,122,136 A | 6/1992 | Guglielmi et al. |
| 5,192,301 A | 3/1993 | Kamiya et al. |
| 5,261,916 A | 11/1993 | Engelson |
| 5,304,195 A | 4/1994 | Twyford, Jr. et al. |
| 5,334,210 A | 8/1994 | Gianturco |
| 5,350,397 A | 9/1994 | Palermo |
| 5,423,829 A | 6/1995 | Pham et al. |
| 5,624,449 A | 4/1997 | Pham et al. |
| 5,645,558 A | 7/1997 | Horton |
| 5,733,294 A | 3/1998 | Forber et al. |
| 5,891,128 A | 4/1999 | Chin et al. |
| 5,916,235 A | 6/1999 | Guglielmi |
| 5,928,260 A | 7/1999 | Chin et al. |
| 5,935,148 A | 8/1999 | Villar |
| 5,941,249 A | 8/1999 | Maynard |
| 5,951,599 A | 9/1999 | McCrory |
| 6,007,573 A | 12/1999 | Wallace et al. |
| 6,024,756 A | 2/2000 | Pham |
| 6,036,720 A | 3/2000 | Abrams |
| 6,063,070 A | 5/2000 | Eder |
| 6,063,100 A | 5/2000 | Diaz et al. |
| 6,063,104 A | 5/2000 | Villar |
| 6,080,191 A | 6/2000 | Thaler |
| 6,086,577 A | 7/2000 | Ken et al. |
| 6,096,021 A | 8/2000 | Helm et al. |
| 6,113,609 A | 9/2000 | Adams |
| 6,123,714 A | 9/2000 | Gia et al. |
| 6,168,615 B1 | 1/2001 | Ken |
| 6,168,622 B1 | 1/2001 | Mazzocchi |
| 6,221,086 B1 | 4/2001 | Forber |
| 6,270,515 B1 | 8/2001 | Linden et al. |
| 6,315,787 B1 | 11/2001 | Tsugita et al. |
| 6,331,184 B1 | 12/2001 | Abrams |
| 6,334,048 B1 | 12/2001 | Edvardsson et al. |
| 6,346,117 B1 | 2/2002 | Greenhalgh |
| 6,350,270 B1 | 2/2002 | Roue |
| 6,375,606 B1 | 4/2002 | Garibaldi et al. |
| 6,375,668 B1 | 4/2002 | Gifford |
| 6,379,329 B1 | 4/2002 | Naglreiter et al. |
| 6,391,037 B1 | 5/2002 | Greenhalgh |
| 6,419,686 B1 | 7/2002 | McLeod et al. |
| 6,428,558 B1 | 8/2002 | Jones |
| 6,454,780 B1 | 9/2002 | Wallace |
| 6,463,317 B1 | 10/2002 | Kucharczyk et al. |
| 6,506,204 B2 | 1/2003 | Mazzocchi et al. |
| 6,527,919 B1 | 3/2003 | Roth |
| 6,547,804 B2 | 4/2003 | Porter et al. |
| 6,551,303 B1 | 4/2003 | Van Tassel et al. |
| 6,569,179 B2 | 5/2003 | Teoh |
| 6,569,190 B2 | 5/2003 | Whalen, II et al. |
| 6,572,628 B2 | 6/2003 | Dominguez |
| 6,589,230 B2 | 7/2003 | Gia et al. |
| 6,589,256 B2 | 7/2003 | Forber |
| 6,605,102 B1 | 8/2003 | Mazzocchi et al. |
| 6,620,152 B2 | 9/2003 | Guglielmi |
| 6,669,719 B2 | 12/2003 | Wallace et al. |
| 6,689,159 B2 | 2/2004 | Lilip Lau et al. |
| 6,746,468 B1 | 6/2004 | Sepetka |
| 6,780,196 B2 | 8/2004 | Chin et al. |
| 6,802,851 B2 | 10/2004 | Jones |
| 6,811,560 B2 | 11/2004 | Jones |
| 6,833,003 B2 | 12/2004 | Jones et al. |
| 6,846,316 B2 | 1/2005 | Abrams |
| 6,855,154 B2 | 2/2005 | Abdel-Gawwad |
| 6,949,116 B2 | 9/2005 | Solymar et al. |
| 6,964,671 B2 | 11/2005 | Cheng |
| 7,044,134 B2 | 5/2006 | Khairkhahan et al. |
| 7,083,632 B2 | 8/2006 | Avellanet |
| 7,093,527 B2 | 8/2006 | Rapaport et al. |
| 7,128,736 B1 | 10/2006 | Abrams et al. |
| 7,152,605 B2 | 12/2006 | Khairkhahan et al. |
| 7,153,323 B1 | 12/2006 | Teoh |
| 7,195,636 B2 | 3/2007 | Avellanet et al. |
| 7,229,454 B2 | 6/2007 | Tran et al. |
| 7,229,461 B2 | 6/2007 | Chin et al. |
| 7,309,345 B2 | 12/2007 | Wallace |
| 7,371,249 B2 | 5/2008 | Douk et al. |
| 7,410,482 B2 | 8/2008 | Murphy et al. |
| 7,572,288 B2 | 8/2009 | Cox |
| 7,597,704 B2 | 10/2009 | Frazier et al. |
| 7,608,088 B2 | 10/2009 | Jones |
| 7,695,488 B2 | 4/2010 | Berenstein et al. |
| 7,713,264 B2 | 5/2010 | Murphy |
| 7,744,652 B2 | 6/2010 | Morsi |
| 7,892,248 B2 | 2/2011 | Tran |
| RE42,758 E | 9/2011 | Ken |
| 8,016,852 B2 | 9/2011 | Ho |
| 8,021,416 B2 | 9/2011 | Abrams |
| 8,025,668 B2 | 9/2011 | McCartney |
| 8,034,061 B2 | 10/2011 | Amplatz et al. |
| 8,048,145 B2 | 11/2011 | Evans et al. |
| 8,075,585 B2 | 12/2011 | Lee et al. |
| 8,142,456 B2 | 3/2012 | Rosqueta et al. |
| 8,221,483 B2 | 7/2012 | Ford et al. |
| 8,261,648 B1 | 9/2012 | Marchand et al. |
| 8,267,923 B2 | 9/2012 | Murphy |
| 8,361,106 B2 | 1/2013 | Solar et al. |
| 8,361,138 B2 | 1/2013 | Adams |
| 8,372,114 B2 | 2/2013 | Hines |
| 8,398,671 B2 | 3/2013 | Chen |
| 8,430,012 B1 | 4/2013 | Marchand |
| 8,454,633 B2 | 6/2013 | Amplatz et al. |
| 8,523,897 B2 | 9/2013 | van der Burg et al. |
| 8,777,974 B2 | 7/2014 | Amplatz et al. |
| 8,974,512 B2 | 3/2015 | Aboytes et al. |
| 8,992,568 B2 | 3/2015 | Duggal et al. |
| 8,998,947 B2 | 4/2015 | Aboytes et al. |
| 9,055,948 B2 | 6/2015 | Jaeger et al. |
| 9,107,670 B2 | 8/2015 | Hannes |
| 9,232,992 B2 | 1/2016 | Heidner et al. |
| 9,314,326 B2 | 4/2016 | Wallace et al. |
| 9,351,715 B2 | 5/2016 | Mach |
| 9,414,842 B2 | 8/2016 | Glimsdale et al. |
| 9,526,813 B2 | 12/2016 | Cohn et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,096 B2 | 2/2017 | Fogarty |
| 9,561,125 B2 | 2/2017 | Bowman et al. |
| 9,572,982 B2 | 2/2017 | Burnes et al. |

(56) References Cited

U.S. PATENT DOCUMENTS

| | | |
|---|---|---|
| 9,579,484 B2 | 2/2017 | Barnell |
| 9,585,642 B2 | 3/2017 | Dinsmoor et al. |
| 9,585,669 B2 | 3/2017 | Becking et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign |
| 9,681,861 B2 | 6/2017 | Heisel et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li |
| 9,775,621 B2 | 10/2017 | Tompkins et al. |
| 9,775,706 B2 | 10/2017 | Paterson |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman |
| 9,833,252 B2 | 12/2017 | Sepetka |
| 9,833,604 B2 | 12/2017 | Lam |
| 9,833,625 B2 | 12/2017 | Waldhauser et al. |
| 9,918,720 B2 | 3/2018 | Marchand et al. |
| 9,955,976 B2 | 5/2018 | Hewitt et al. |
| 10,130,372 B2 | 11/2018 | Griffin |
| 10,307,148 B2 | 6/2019 | Heisel et al. |
| 10,327,781 B2 | 6/2019 | Divino et al. |
| 10,342,546 B2 | 7/2019 | Sepetka et al. |
| 10,716,573 B2 | 7/2020 | Connor |
| 2002/0068974 A1 | 6/2002 | Kuslich et al. |
| 2002/0082638 A1 | 6/2002 | Porter et al. |
| 2002/0143349 A1 | 10/2002 | Gifford, III et al. |
| 2002/0188314 A1 | 12/2002 | Anderson et al. |
| 2003/0028209 A1 | 2/2003 | Teoh et al. |
| 2003/0120337 A1 | 6/2003 | Van Tassel et al. |
| 2003/0171739 A1* | 9/2003 | Murphy ............ A61B 17/12022 606/1 |
| 2003/0176884 A1 | 9/2003 | Berrada et al. |
| 2003/0181927 A1 | 9/2003 | Wallace |
| 2003/0181945 A1 | 9/2003 | Opolski |
| 2003/0195553 A1 | 10/2003 | Wallace |
| 2003/0216772 A1 | 11/2003 | Konya |
| 2004/0034366 A1 | 2/2004 | van der Burg et al. |
| 2004/0044391 A1 | 3/2004 | Porter |
| 2004/0087998 A1 | 5/2004 | Lee et al. |
| 2004/0098027 A1 | 5/2004 | Teoh et al. |
| 2004/0127935 A1 | 7/2004 | Van Tassel et al. |
| 2004/0133222 A1 | 7/2004 | Tran et al. |
| 2004/0153120 A1 | 8/2004 | Seifert et al. |
| 2004/0254594 A1 | 12/2004 | Alfaro |
| 2005/0021016 A1 | 1/2005 | Malecki et al. |
| 2005/0159771 A1 | 7/2005 | Petersen |
| 2005/0177103 A1 | 8/2005 | Hunter et al. |
| 2005/0251200 A1 | 11/2005 | Porter |
| 2006/0052816 A1 | 3/2006 | Bates et al. |
| 2006/0058735 A1 | 3/2006 | Lesh |
| 2006/0064151 A1 | 3/2006 | Guterman et al. |
| 2006/0106421 A1 | 5/2006 | Teoh |
| 2006/0155323 A1 | 7/2006 | Porter et al. |
| 2006/0155367 A1 | 7/2006 | Hines |
| 2006/0167494 A1 | 7/2006 | Suddaby |
| 2006/0247572 A1 | 11/2006 | McCartney |
| 2007/0106311 A1 | 5/2007 | Wallace et al. |
| 2007/0208376 A1 | 6/2007 | Meng |
| 2007/0162071 A1 | 7/2007 | Burkett et al. |
| 2007/0173928 A1 | 7/2007 | Morsi |
| 2007/0186933 A1 | 8/2007 | Domingo |
| 2007/0265656 A1 | 11/2007 | Amplatz et al. |
| 2007/0288083 A1 | 12/2007 | Hines |
| 2008/0097495 A1 | 4/2008 | Feller, III et al. |
| 2008/0281350 A1* | 11/2008 | Sepetka ............ A61B 17/0057 606/200 |
| 2009/0062841 A1 | 3/2009 | Amplatz et al. |
| 2009/0099647 A1 | 4/2009 | Glimsdale |
| 2009/0281557 A1 | 11/2009 | Sander et al. |
| 2009/0287297 A1 | 11/2009 | Cox |
| 2009/0318941 A1 | 12/2009 | Sepetka |
| 2010/0023046 A1 | 1/2010 | Heidner et al. |
| 2010/0023048 A1 | 1/2010 | Mach |
| 2010/0063573 A1 | 3/2010 | Hijlkema |
| 2010/0063582 A1 | 3/2010 | Rudakov |
| 2010/0069948 A1 | 3/2010 | Veznedaroglu et al. |
| 2010/0168781 A1 | 7/2010 | Berenstein |
| 2010/0324649 A1 | 12/2010 | Mattsson et al. |
| 2011/0046658 A1 | 2/2011 | Conner et al. |
| 2011/0054519 A1 | 3/2011 | Neuss |
| 2011/0152993 A1 | 6/2011 | Marchand et al. |
| 2011/0196413 A1 | 8/2011 | Wallace |
| 2011/0319978 A1 | 12/2011 | Schaffer |
| 2012/0010644 A1 | 1/2012 | Sideris et al. |
| 2012/0071911 A1 | 3/2012 | Sadasivan |
| 2012/0283768 A1 | 12/2012 | Cox et al. |
| 2012/0310270 A1 | 12/2012 | Murphy |
| 2012/0330341 A1 | 12/2012 | Becking et al. |
| 2013/0035665 A1 | 2/2013 | Chu |
| 2013/0035712 A1 | 2/2013 | Theobald et al. |
| 2013/0066357 A1 | 3/2013 | Aboytes et al. |
| 2013/0079864 A1 | 3/2013 | Boden |
| 2013/0110066 A1 | 5/2013 | Sharma et al. |
| 2013/0204351 A1 | 8/2013 | Cox et al. |
| 2013/0211495 A1* | 8/2013 | Halden ............ A61B 17/12022 623/1.12 |
| 2013/0261730 A1 | 10/2013 | Bose et al. |
| 2013/0345738 A1 | 12/2013 | Eskridge |
| 2014/0012307 A1 | 1/2014 | Franano et al. |
| 2014/0012363 A1 | 1/2014 | Franano et al. |
| 2014/0018838 A1 | 1/2014 | Franano et al. |
| 2014/0135812 A1 | 5/2014 | Divino et al. |
| 2014/0200607 A1 | 7/2014 | Sepetka et al. |
| 2014/0257360 A1 | 9/2014 | Keillor |
| 2014/0277013 A1* | 9/2014 | Sepetka ............ A61B 17/221 606/159 |
| 2015/0209050 A1 | 7/2015 | Aboytes et al. |
| 2015/0272589 A1 | 10/2015 | Lorenzo |
| 2015/0313605 A1 | 11/2015 | Griffin |
| 2015/0342613 A1 | 12/2015 | Aboytes et al. |
| 2015/0374483 A1 | 12/2015 | Janardhan et al. |
| 2016/0022445 A1 | 1/2016 | Ruvalcaba et al. |
| 2016/0030050 A1 | 2/2016 | Franano et al. |
| 2016/0192912 A1 | 7/2016 | Kassab et al. |
| 2016/0249934 A1 | 9/2016 | Hewitt et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu |
| 2017/0027640 A1 | 2/2017 | Kunis et al. |
| 2017/0027692 A1 | 2/2017 | Bonhoeffer |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |

(56) References Cited

U.S. PATENT DOCUMENTS

| | | |
|---|---|---|
| 2017/0071737 A1 | 3/2017 | Kelley |
| 2017/0072452 A1 | 3/2017 | Monetti et al. |
| 2017/0079661 A1* | 3/2017 | Bardsley .......... A61B 17/12113 |
| 2017/0079662 A1* | 3/2017 | Rhee ................ A61B 17/12031 |
| 2017/0079671 A1 | 3/2017 | Morero |
| 2017/0079680 A1 | 3/2017 | Bowman |
| 2017/0079717 A1 | 3/2017 | Walsh et al. |
| 2017/0079766 A1 | 3/2017 | Wang |
| 2017/0079767 A1 | 3/2017 | Leon-Yip |
| 2017/0079812 A1 | 3/2017 | Lam et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo |
| 2017/0113023 A1 | 4/2017 | Steingisser et al. |
| 2017/0114350 A1 | 4/2017 | dos Santos et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein |
| 2017/0165454 A1 | 6/2017 | Tuohy |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh |
| 2017/0303942 A1 | 10/2017 | Greenhalgh et al. |
| 2017/0303947 A1 | 10/2017 | Greenhalgh |
| 2017/0303948 A1 | 10/2017 | Wallace |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |
| 2017/0340383 A1 | 11/2017 | Bloom et al. |
| 2017/0348014 A1 | 12/2017 | Wallace |
| 2017/0348514 A1 | 12/2017 | Guyon et al. |
| 2018/0140305 A1 | 5/2018 | Connor |
| 2018/0242979 A1 | 8/2018 | Lorenzo |
| 2018/0338767 A1 | 11/2018 | Dasnurkar et al. |
| 2019/0008522 A1 | 1/2019 | Lorenzo |
| 2019/0223878 A1 | 1/2019 | Lorenzo et al. |
| 2019/0192162 A1 | 6/2019 | Lorenzo |
| 2019/0192167 A1 | 6/2019 | Lorenzo |
| 2019/0192168 A1 | 6/2019 | Lorenzo |
| 2019/0328398 A1 | 10/2019 | Lorenzo |
| 2019/0365385 A1 | 12/2019 | Gorochow et al. |

FOREIGN PATENT DOCUMENTS

| | | |
|---|---|---|
| CA | 2598048 A1 | 5/2008 |
| CN | 204 683 687 U | 7/2015 |
| DE | 102008015781 A1 | 10/2009 |
| DE | 102010053111 A1 | 6/2012 |
| DE | 102009058132 B4 | 7/2014 |
| DE | 10 2013 106031 A1 | 12/2014 |
| DE | 202008018523 U1 | 4/2015 |
| DE | 102011102955 B4 | 5/2018 |
| EP | 0902704 B1 | 3/1999 |
| EP | 1054635 B1 | 11/2000 |
| EP | 1295563 B1 | 3/2003 |
| EP | 1441649 B1 | 8/2004 |
| EP | 1483009 B1 | 12/2004 |
| EP | 1527753 B1 | 5/2005 |
| EP | 1569565 B1 | 9/2005 |
| EP | 1574169 B1 | 9/2005 |
| EP | 1494619 B1 | 1/2006 |
| EP | 1633275 B1 | 3/2006 |
| EP | 1659988 B1 | 5/2006 |
| EP | 1725185 B1 | 11/2006 |
| EP | 1862122 A1 | 12/2007 |
| EP | 1923005 B1 | 5/2008 |
| EP | 2063791 B1 | 6/2009 |
| EP | 2134263 B1 | 12/2009 |
| EP | 2157937 B1 | 3/2010 |
| EP | 2266456 A1 | 12/2010 |
| EP | 2324775 B1 | 5/2011 |
| EP | 2367482 B1 | 9/2011 |
| EP | 2387951 B1 | 11/2011 |
| EP | 2460476 A2 | 6/2012 |
| EP | 2468349 A1 | 6/2012 |
| EP | 2543345 A1 | 1/2013 |
| EP | 2567663 A1 | 3/2013 |
| EP | 2617386 A1 | 7/2013 |
| EP | 2647343 A2 | 10/2013 |
| EP | 2848211 A1 | 3/2015 |
| EP | 2854704 B1 | 4/2015 |
| EP | 2923674 B1 | 9/2015 |
| EP | 2926744 A1 | 10/2015 |
| EP | 3146916 A1 | 3/2017 |
| EP | 3501429 A1 | 6/2019 |
| EP | 3517055 A1 | 7/2019 |
| JP | H04-47415 U | 4/1992 |
| JP | H07-37200 U | 7/1995 |
| JP | 2006-509578 A | 3/2006 |
| JP | 2013-509972 A | 3/2013 |
| JP | 2013537069 A | 9/2013 |
| JP | 2016-502925 A | 2/2015 |
| WO | 9641589 A1 | 12/1996 |
| WO | 99/05977 A1 | 2/1999 |
| WO | 9908607 A1 | 2/1999 |
| WO | 99/30640 | 6/1999 |
| WO | 2003073961 A1 | 9/2003 |
| WO | 2005020822 A1 | 3/2005 |
| WO | 2005/074814 A2 | 8/2005 |
| WO | 2005/117718 A1 | 12/2005 |
| WO | 2005117718 A1 | 12/2005 |
| WO | 2006034149 A2 | 3/2006 |
| WO | 2006052322 A2 | 5/2006 |
| WO | 2007/076480 A2 | 7/2007 |
| WO | 2008150346 A1 | 12/2008 |
| WO | WO 2008151204 A1 | 12/2008 |
| WO | 2009048700 A1 | 4/2009 |
| WO | 2009105365 A1 | 8/2009 |
| WO | 2009132045 A2 | 10/2009 |
| WO | 2009135166 A2 | 11/2009 |
| WO | 2010030991 A1 | 3/2010 |
| WO | 2011057002 A2 | 5/2011 |
| WO | 2012032030 A1 | 3/2012 |
| WO | 2012099704 A2 | 7/2012 |
| WO | 2012099909 A2 | 7/2012 |
| WO | 2012113554 A1 | 8/2012 |
| WO | 2013016618 A2 | 1/2013 |

(56) References Cited

FOREIGN PATENT DOCUMENTS

| WO | 2013025711 A1 | 2/2013 |
|----|---------------|--------|
| WO | 2013109309 A1 | 7/2013 |
| WO | 2013159065 A1 | 10/2013 |
| WO | 2014029835 A1 | 2/2014 |
| WO | 2014110589 A1 | 7/2014 |
| WO | 2014137467 A1 | 9/2014 |
| WO | 2015073704 A1 | 5/2015 |
| WO | 2015/160721 A1 | 10/2015 |
| WO | 2015160721 A1 | 10/2015 |
| WO | 2015/171268 A2 | 11/2015 |
| WO | 2015166013 A1 | 11/2015 |
| WO | 2015171268 A2 | 11/2015 |
| WO | 2015184075 A1 | 12/2015 |
| WO | 2015187196 A1 | 12/2015 |
| WO | 2016/044647 A2 | 3/2016 |
| WO | 2016107357 A1 | 7/2016 |
| WO | 2016/137997 | 9/2016 |
| WO | 2018/051187 A1 | 3/2018 |

OTHER PUBLICATIONS

Extended European Search Report issued in corresponding European Patent Application No. 19 21 5277 dated May 12, 2020.
Altes et al., Creation of Saccular Aneurysms in the Rabbit: A Model Suitable for Testing Endovascular Devices. AJR 2000; 174: 349-354.
Schaffer, Advanced Materials & Processes, Oct. 2002, pp. 51-54.

\* cited by examiner

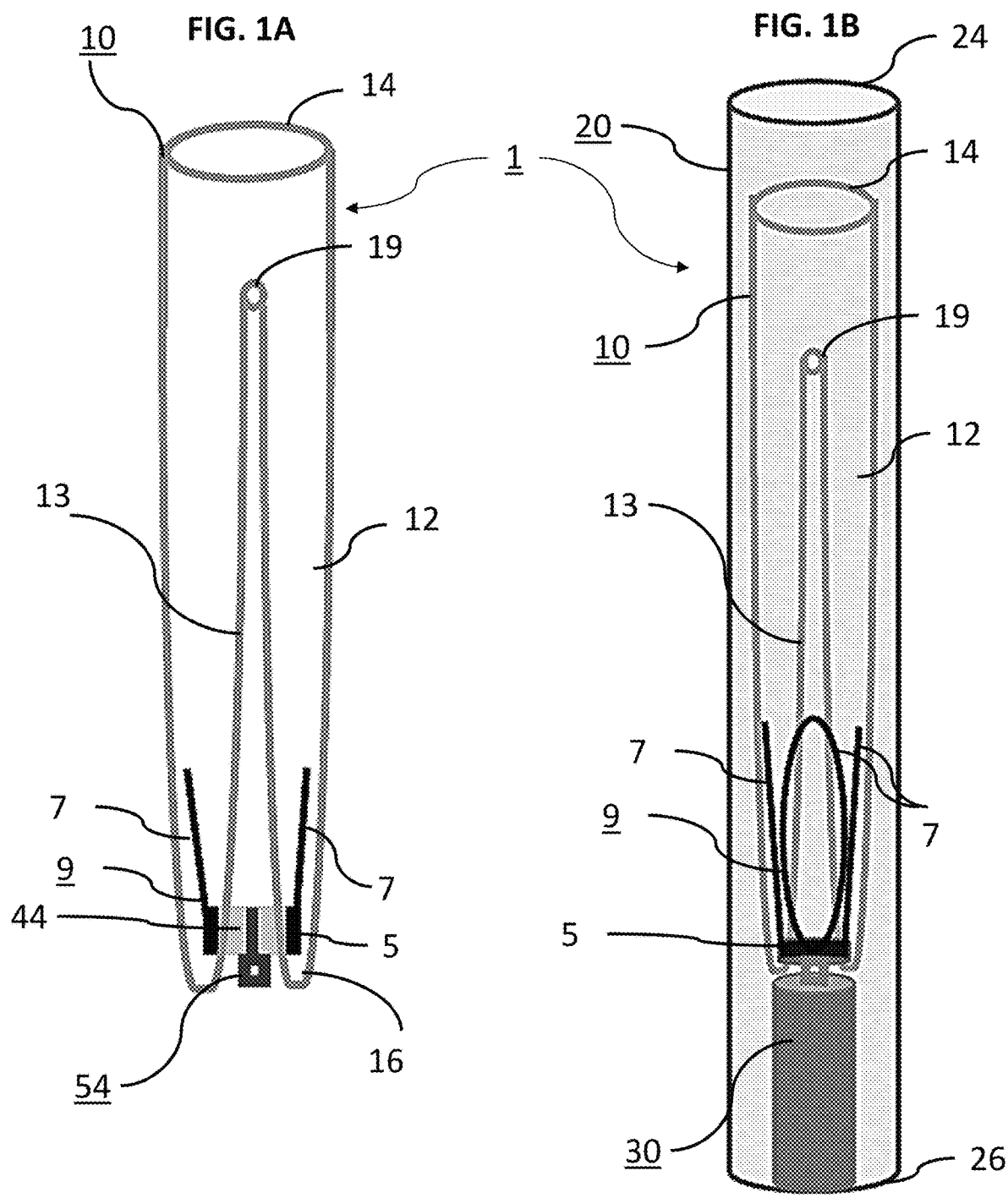

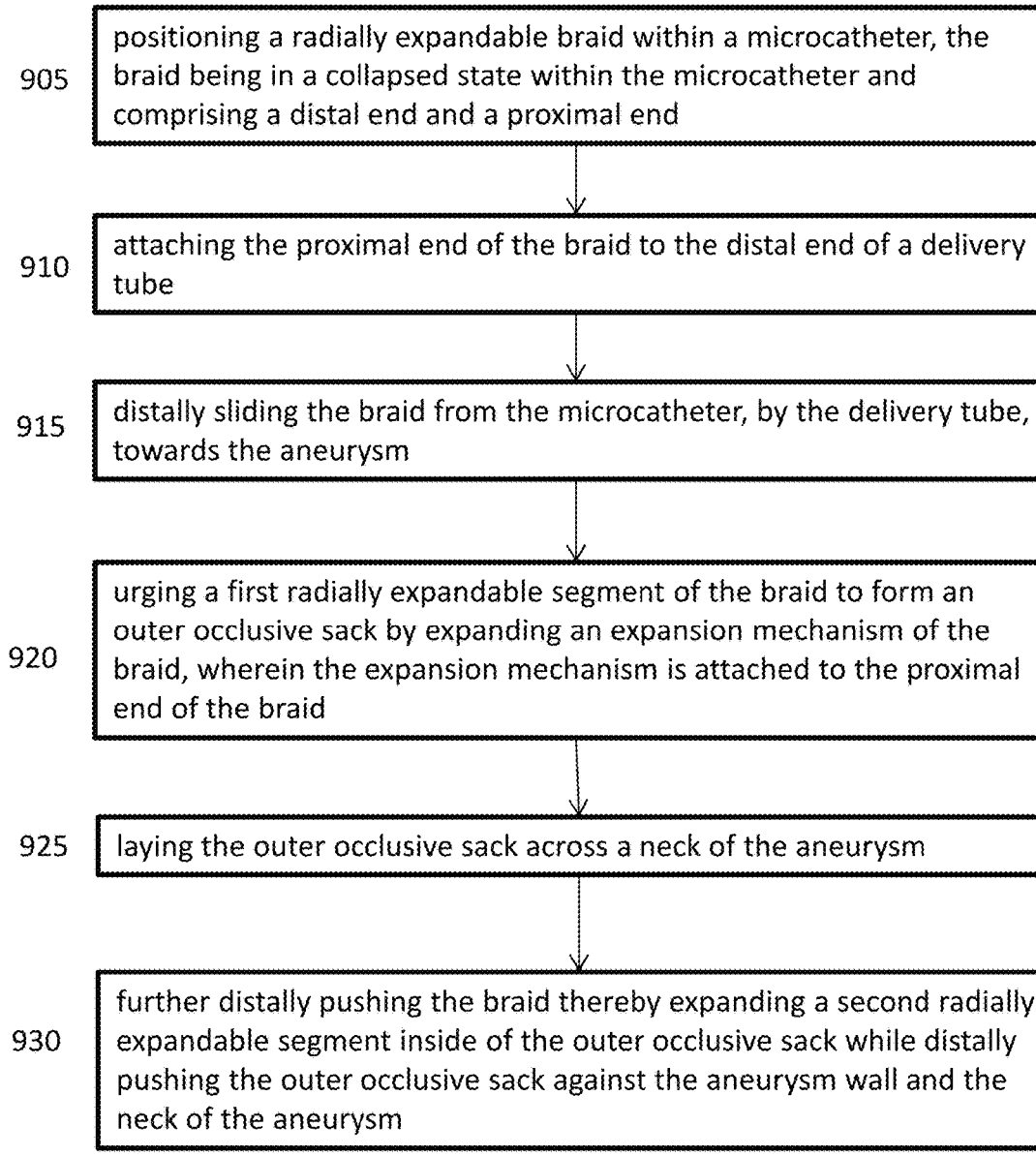

ANEURYSM DEVICE AND DELIVERY SYSTEM

FIELD

This disclosure relates to medical instruments, and more particularly, systems and devices for aneurysm therapy.

BACKGROUND

Aneurysms can be complicated and difficult to treat. For example, treatment access may be limited or unavailable when an aneurysm is located proximate critical tissues. Such factors are of particular concern with cranial aneurysms due to the brain tissue surrounding cranial vessels the corresponding limited treatment access.

Prior solutions have included endovascular treatment access whereby an internal volume of the aneurysm sac is removed or excluded from arterial blood pressure and flow. In this respect, because the interior walls of the aneurysm may continue being subjected to flow of blood and related pressure, aneurysm rupture remains possible.

Alternative to endovascular or other surgical approaches can include occlusive devices. Such devices have typically incorporated multiple embolic coils that are delivered to the vasculature using microcatheter delivery systems. For example, when treating cranial aneurysms, a delivery catheter with embolic coils is typically first inserted into non-cranial vasculature through a femoral artery in the hip or groin area. Thereafter, the catheter is guided to a location of interest within the cranium. The sac of the aneurysm can then be filled with the embolic material to create a thrombotic mass that protects the arterial walls from blood flow and related pressure. However, such occlusive devices do have certain shortcomings, including mass effect, which can cause compression on the brain and its nerves.

One particular type of occlusive approach endeavors to deliver and treat the entrance or "neck" of the aneurysm as opposed to the volume of the aneurysm. In such "neck" approaches, by minimizing blood flow across the neck, then a cessation of flow into the aneurysm may be achieved. In turn, a thrombotic mass may naturally form without having to deliver embolic materials, as previously described. This is preferable to masses formed from embolic material since a natural mass can improve healing by reducing possible distention from arterial walls and permits reintegration into the original parent vessel shape along the neck plane of the aneurysm. It is understood that the neck plane is an imaginary surface where the inner most layer of the parent wall would be but for the aneurysm. However, neck-occlusive approaches are not without drawbacks. It is desired to block the neck of the aneurysm in the parent vessel. Furthermore, embolic coils do not always effectively treat aneurysms as re-canalization of the aneurysm and/or coil compaction can occur over time.

It is therefore desirable to have a device which easily, accurately, and safely occludes a neck of an aneurysm or other arterio-venous malformation in a parent vessel without blocking flow into perforator vessels communicating with the parent vessel.

SUMMARY

In some embodiments, the present disclosure relates to a braid for treating an aneurysm. The braid can include a first radially expandable segment operable to move from a collapsed state within a microcatheter to a deployed state distal of the microcatheter. The first radially expandable segment can be capable of radially expanding to form an outer occlusive sack in the aneurysm that seals the neck of the aneurysm in the deployed state. The braid can also include a second radially expandable segment operable to move from the collapsed state within the microcatheter to the deployed state distal of the microcatheter, wherein the second radially expandable segment is capable of radially expanding inside the outer occlusive sack to form an inner occlusive sack in the outer occlusive sack in the deployed state. An expansion mechanism can be included and be disposed at a proximal end of the first and second radially expandable segments.

In some embodiments, the expansion mechanism can include an expansion ring with an opening. A distal end of the braid can be inserted through the opening and then the proximal end can be folded over the opening.

In some embodiments, the expansion mechanism can include an opening and a plurality of radially flexible elements. Each flexible element can be capable of expanding from a collapsed condition in the microcatheter to an expanded condition in the deployed state distal of the microcatheter to support a proximal portion of the outer occlusive sack. Each radially flexible element can be evenly radially spaced about a central axis of the expansion mechanism. The central axis of the expansion mechanism can be axially aligned with a central axis of the first and second radially expandable segments.

In some embodiments, the expansion mechanism can include at least four radially spaced flexible elements that extend from an expansion ring (e.g. a radially movable leaf capable of moving between collapsed to deployed conditions). However, the solution is not so limited any instead greater or fewer than four leaves can be included, as needed or required.

In some embodiments, the expansion ring and leaf or leaves can be a monolithic structure. The expansion ring and leaf or leaves can also be formed from a memory alloy material such as nitinol.

In some embodiments, the expansion mechanism can include a plurality of expandable support elements that include potential energy stored in the collapsed state (e.g. the support elements may include biased bias elements or be memory shaped to expand a predetermined manner and release a predetermined amount of potential energy). The expandable support elements can be configured to urge the proximal end of the first radially expandable segment from the collapsed to the deployed state by releasing the potential energy of the expandable support elements.

In some embodiments, a porosity of the inner occlusive sack is greater than a porosity of the outer occlusive sack.

In some embodiments, distally translating the braid after the outer occlusive sack is formed causes an inner layer of the braid inside of the outer occlusive sack to radially expand inside the outer occlusive sack and form the inner occlusive sack. The inner layer of the braid can also be capable of radially expanding inside the outer occlusive sack while the outer occlusive sack is pushed against the aneurysm wall and aneurysm neck.

In some embodiments, a marker band can be included and in communication with the proximal end of the braid. The inner layer that radially expands inside the outer occlusive sack can also be formed by folding the proximal end over the marker band.

In some embodiments, wherein in the deployed state, the braid is detachable from a delivery system in the aneurysm.

In some embodiments, the delivery system can include a microcatheter and a delivery tube. The distal end of the delivery tube can be detachably connected to the proximal end of the braid. The delivery tube can be translatably disposable within the microcatheter. The delivery tube can also be capable of distally translating the braid within the microcatheter from the collapsed state to the deployed state.

In some embodiments, the outer occlusive sack can be a collapsible cage-like vaso-occlusive structure.

In some embodiments, the outer occlusive sack can include fewer wire segments than the inner occlusive sack.

In some embodiments, dimensions of interstices of the braid vary at the proximal end versus the distal end so that a porosity of the outer occlusive sack is less than a porosity of the inner occlusive sack.

In some embodiments, the braid can be included in a system or otherwise in communication with an imaging device capable of imaging the outer and/or inner occlusive sacks with respect to the aneurysm. An orientation of the outer and/or inner occlusive sacks can be adjustable by the braid being distally or proximally moved.

In some embodiments, an occlusive device for treating an aneurysm is provided. The device can include a braid being translatably disposable within a microcatheter from a collapsed state to a deployed state. The braid can include a distal end and a proximal end. In the deployed state, the braid can include an outer occlusive sack capable of pushing against an aneurysm wall of the aneurysm and sealing a neck of the aneurysm to deflect, divert, and/or slow a flow into the aneurysm, an inner occlusive sack disposed inside the outer occlusive sack, and an expansion mechanism disposed at the proximal end for urging formation of the outer and/or inner occlusive sacks in the deployed state.

In other embodiments, a method of occluding an aneurysm is disclosed. The method can include one or more of the following steps: positioning a radially expandable braid within a microcatheter, the braid being in a collapsed state within the microcatheter and comprising a distal end and a proximal end; attaching the proximal end of the braid to the distal end of a delivery tube; distally sliding the braid from the microcatheter, by the delivery tube, towards an aneurysm; urging a first radially expandable segment of the braid to form an outer occlusive sack by expanding an expansion mechanism of the braid, wherein the expansion mechanism is attached to the proximal end of the braid; laying the outer occlusive sack across a neck of the aneurysm; and further distally pushing the braid thereby expanding a second radially expandable segment inside of the outer occlusive sack while distally pushing the outer occlusive sack against the aneurysm wall and the neck of the aneurysm.

In certain embodiments, the method can include releasing the braid, including the outer and inner occlusive sacks, and withdrawing the delivery tube and the microcatheter from the aneurysm.

In certain embodiments, the expansion mechanism includes a plurality of radially spaced flexible elements, each flexible element capable of expanding from a collapsed condition in the microcatheter to an expanded condition in the deployed state to support a proximal portion of the outer occlusive sack. In this respect, the method can also include axially aligning the central axis of the expansion mechanism with a central axis of the first and second radially expandable segments; and radially spacing each flexible element about the central axis of the expansion mechanism.

In some embodiments, the method can include providing an expansion ring with an opening on or with the expansion mechanism; inserting a distal end of the braid through the opening; and folding the proximal end of the braid over the opening.

In some embodiments, the method can include radially spacing, about the expansion mechanism, at least four flexible elements that extend from an expansion ring, each flexible element being a radially movable leaf capable of moving between collapsed to deployed conditions.

In some embodiments, the method can include forming a monolithic structure from the expansion ring and the at least four flexible elements.

In some embodiments, the method can include forming a plurality of expandable support elements on the expansion mechanism that comprise potential energy stored in the collapsed state; and urging, by the expandable support elements, the proximal end of the first radially expandable segment from the collapsed to the deployed state by releasing the potential energy.

In some embodiments, the method can include forming the first radially expandable segment with a porosity lower than a porosity of the second radially expandable segment; positioning the first radially expandable segment adjacent or in communication with a neck of the aneurysm; and deflecting, diverting, and/or slowing a flow into the aneurysm.

Other aspects and features of the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

FIG. 1A depicts an example occlusive device of this disclosure in a collapsed state.

FIG. 1B depicts an example occlusive device of this disclosure in a collapsed state within an example microcatheter.

FIG. 9 is a flow diagram for a method of delivering an occlusive device

DETAILED DESCRIPTION

Figure 2A:
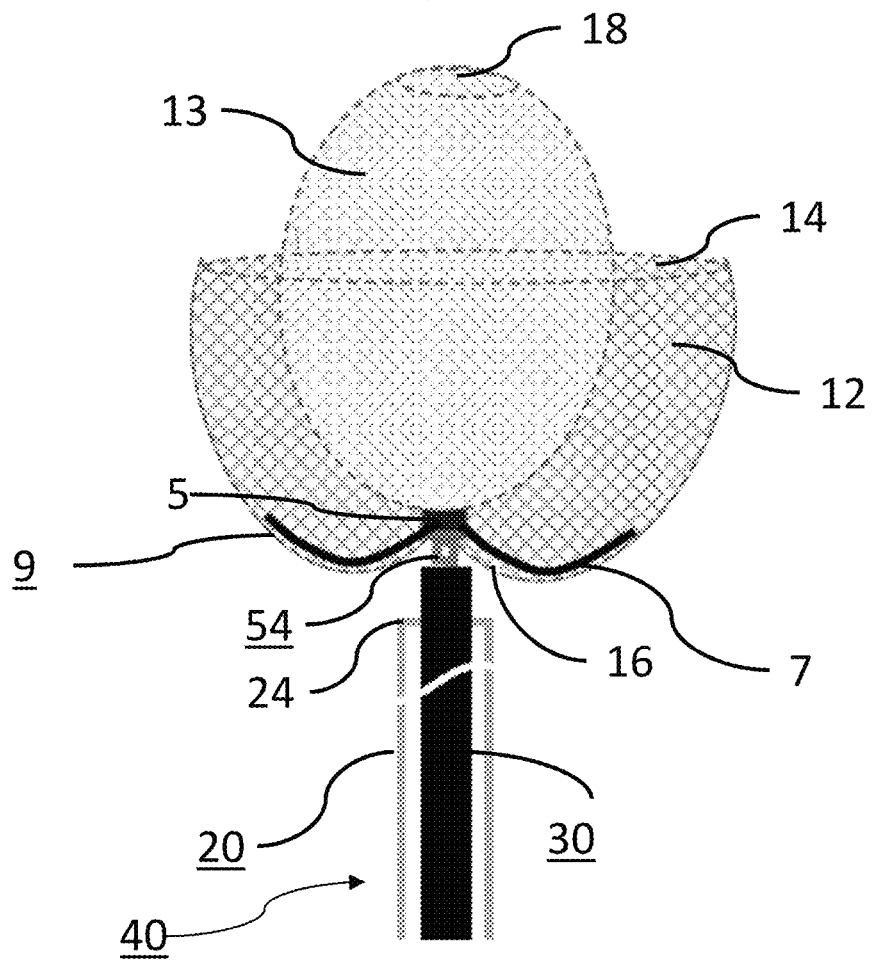
FIG. 2A is a schematic side view of an exemplary delivery system with an occlusive device in a deployed state but not delivered to the aneurysm.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, vasculature can be that of any "subject" or "patient" including of any human or animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g., rat, dog, pig, monkey, or the like). It should be appreciated that the subject may be any applicable human patient, for example.

As discussed herein, "operator" may include a doctor, surgeon, or any other individual or delivery instrumentation associated with delivery of a braid body to the vasculature of a subject.

Relatedly, flow diverters that are deployed across the aneurysm neck can alter the flow of blood into the aneurysm. An example flow diverter can be a braided device with relatively low porosity. Over time, the aneurysms can heal by sealing the aneurysm neck with a high rate of success. However, flow diversion technology is not without limitations. Challenges include placement of the devices intravascularly due to vessel morphology, vessel tortuosity, or braid malposition. In addition, patients receiving a flow diverter must be on anticoagulation medicine for an extended period to prevent vessel thrombosis. Intravascular devices also aim to cut circulation into the aneurysm while minimizing the amount of metal in the vessel and significantly cutting, or eliminating the need for coagulation medication. These types of devices may also be easier to track and/or deploy at the lesion site.

The occlusive device 1 disclosed herein addresses these and other drawbacks of previous approaches by using a single device to seal the aneurysm neck. Turning to FIG. 1A, an example occlusive device 1 of this disclosure is shown in a collapsed state prior to being arranged with a microcatheter 20. FIG. 1B depicts the occlusive device of FIG. 1A arranged in the collapsed state within the microcatheter 20. As shown, device 1 can include a braid 10 formed from multiple self-expanding multi-filament segments that can be formed from a mesh. For example, braid 10 can include a first radially expandable segment 12 associated with an outer occlusive sack and a second radially expandable segment 13 associated with an inner occlusive sack. Braid 10 can also have a distal end 14 associated with segment 12, a distal end 18 associated with segment 13, and a proximal end 16.

An expansion mechanism 9 can also be included disposed at or about proximal end 16 of braid 10. The expansion mechanism 9 can include one or more flexible support elements 7 that extend from or are attached to an expansion ring 5 with an opening 3. As shown, the flexible support elements 7 can be oriented to extend along the inner layer of braid 10 in both the collapsed and deployed states. Each flexible support element 7 of mechanism 9 can be elongate and extend at one or more depths into braid 10. Each element 7 of mechanism 9 can facilitate expansion of braid 10 to form sacks of segments 12 and/or 13, collectively with other flexible elements 7 or individually.

The mesh of braid 10 can be defined by one or more mesh patterns, one or more discrete mesh portions, and/or one or more mesh openings defined by braided filaments. For example, the mesh of braid 10 can include a porosity region associated with an outer occlusive sack formed by braid 10 and another porosity region associated with an inner occlusive sack configured to expand and/or internally overlay the outer occlusive sack. The inner occlusive sack can have a higher porosity than the outer occlusive sack. For example, the mesh of braid 10 shown in FIGS. 1A and 1B can include a different porosity region associated with each of segments 12, 13.

Each of segments 12, 13 can be radially expandable and capable of being disposed inside microcatheter 20 in a collapsed state. Segment 12 can be an expandable, outer shell while segment 13 can be an inner, expandable shell. Segment 12 may expand and only partially file some of the aneurysm as shown and may form a "cup" like shape that within segment 13 can form and expand. Each of segments 12, 13 can be heat shaped to spherical, saddled, ellipsoid shaped, or any other shape, as shown in FIGS. 1A-2B. Though only segments 12, 13 are depicted, any number of segments could be included as needed or required. Each of segments 12, 13 can be capable of being moved from the collapsed state to a deployed state.

In practice, the porosity of segment 12 can permit the outer occlusive sack of segment 12 to take on many shapes prior to, during, or after delivery to aneurysm A. For example, the porosity of segment 12 can be relatively low to permit its sack to flexibly conform to a plurality of different shaped aneurysms. Segment 12 in this respect can have a porosity less than the porosity of segment 13 based on differing aperture sizes of the mesh. The porosities associated with segments 12, 13 and/or any other region or segment of braid 10 can also include a mesh with filaments having a different shape and/or pick count than the filaments in the other porosity regions.

The mesh of braid 10 can be comprised of a tube that is closed at one end (e.g. proximal end 16) and/or opened at opposite distal ends 14 and 18. Braid 10 can be made of several materials such as deposited thin films or of one single material. The mesh of braid 10 can include multiple wires, for example from 4 to 96 wires. The number of wires can be a factor in controlling material properties of the braid 10, including the porosity, shape in the deployed state, flexibility, stiffness, and the like. The combination of the one or more sacks internally overlaid with an outer occlusive sack can be considered when determining the number of wires of the mesh of braid 10 since one sack is inside the other. Further, the outer occlusive sack of segment 12 and/or the inner occlusive sack of segment 13 can be a collapsible cage-like vaso-occlusive structure.

The diameter of the braid 10, and the braid wire count can vary depending the diameter of the device needed to treat the aneurysm, and/or the desired porosity. For example, the distal end 14 of segment 12 can be an open end with a first diameter. The distal end 18 of segment 13 can be an open end with a second diameter that is less than the first diameter in the deployed state. The braid angle of the braid 10 can also be fixed, or vary along the length of braid 10 to create different porosity therealong. For example, to induce formation of the predetermined shape and strength of the occlusive sacks of segments 12 and 13, ends 14 and 18 may be more pliable than end 16, or vice versa, and other segments of braid 10 may vary from most pliable on or about end 14 and/or end 18 and less pliable on or about end 16. In some embodiments, ends 14, 18 can be looped as shown, which is particularly advantageous to ensure that the braid 10 is atraumatic when in contact with the dome of aneurysm A.

The number of wires, braid angle, patterns, or the like, can be used to define the porosities of segments 12, 13. The wires of braid 10 can be made from nitinol with interwoven platinum filaments for radiopacity, or Drawn Filled Tube (DFT) Nitinol with 10 to 40% Platinum. The wires can be made from a nickel-titanium alloy, cobalt chromium alloys, Stainless Steel, Tantalum, and/or other alloys, and/or any other suitable biocompatible materials, or combination of these materials. Also, these materials can be absorbable or non-absorbable by the patient over time. In this respect, the first porosity associated with segment 12 can be less than the second porosity associated with segment 13. Arranging segments 12, 13 in the deployed state, varying the braid properties, and/or positioning segment 12 adjacent or in communication with a neck of the aneurysm can induce a flow diverting effect. Material properties of segments 12, 13 can differ in other respects as well, as needed or required, including heat treatment or covering.

The apertures in the mesh of braid 10 can also create a substantially unitary frame work or mesh. Thus, the apertures may be of any size, shape, or porosity, and may be uniformly or randomly spaced throughout the wall of the mesh of braid 10. The apertures can provide the tubular element of braid 10 with flexibility and also assist in the transformation of the mesh from the collapsed state to the expanded, deployed state, and vice versa.

As shown in FIG. 1B through FIG. 2B, a delivery system 40 can include the microcatheter 20 with a delivery tube 30 slideably disposed therein. The microcatheter 20 can be pre-placed at the level of the aneurysm neck and used to track the device to the aneurysm. The microcatheter 20 size can be selected in consideration of the size, shape, and directionality of the aneurysm or features through which the microcatheter 20 must pass to get to the treatment site. The microcatheter 20 may have a total usable length anywhere from 80 centimeters to 170 centimeters. The microcatheter 20 may have an inner diameter ID of anywhere between 0.015 and 0.032 inches. The outer diameter OD may also range in size and may narrow at either its proximal end or distal end. At its proximal end 26, the microcatheter 20 may be attached to a surgical device, and at its distal end 24 may be operable to be positioned at the neck of the aneurysm A. While the distal end 24 of the microcatheter 20 as shown contains the braid 10, the end 24 may be varied in shape and may curve at an angle.

Delivery tube 30 can be substantially elongate and can extend from the proximal 26 to the distal end 24 of microcatheter 20. Tube 30 can generally run along the inner lumen of microcatheter 20 and may leave a space between its outer surface and the internal surface of microcatheter 20. In turn, delivery tube 30 and microcatheter 30 may be axially aligned. System 40 can deliver braid 10 to a location of interest (e.g. a lesion site) using microcatheter 20. In certain embodiments, microcatheter 20 can be pre-placed at a level of the aneurysm neck and used to track the device 1 to the lesion, for example by tracking marker band 44 that can have radiopaque material. Delivery tube 30 can be in mechanical connection with braid 10 at locking portion 54. As shown more particularly below, locking portion 54 can comprise or be a pusher ring. Braid 10 may be attached to locking portion 54 by slidable attachment, permanent attachment (e.g. crimped, laser, ultrasonic weld, or other sources of heat, adhesive, or the like) or other attachment approaches. When delivery tube 30 is mechanically attached to braid 10 at locking portion 54, distally translating, sliding, or otherwise moving tube 30 towards the aneurysm A can cause braid 10 to begin moving from the collapsed state within microcatheter 20 to its deployed state external to microcatheter 20 with segments 12 and 13.

In the deployed state, some or all of braid 10 is distal of microcatheter 20 so that segments 12, 13 can radially expand. Braid 10 is particularly advantageous as it is capable of being collapsed within microcatheter 20 and also can form multiple occlusive sacks in the deployed state. The mesh of braid 10 can be configured with or without mechanism 9 so that as braid 10 is distally translated and its end 14 exits from within microcatheter 20, mechanism 9 can urge segment 12 to radially expand to form an outer occlusive sack of the first porosity. The outer occlusive sack of segment 12 can be formed as portions of flexible support elements 7 of mechanism 9 are distal of end 24 and end 14 of braid 10 slides away from end 24 of microcatheter 20. When flexible support elements 7 of mechanism 9 are no longer contained completely within microcatheter 20, they can then release potential energy stored therein and facilitate formation of the occlusive sacks of segments 12 and/or 13.

As braid 10 is further distally translated, segment 13 can begin to radially expand internal to the outer occlusive sack of segment 12. By radially expanding inside segment 12, segment 13 can form an inner occlusive sack with a porosity greater than the porosity of segment 12. As shown in FIG. 2A, the respective sacks of segments 12, 13 are formed now deployed and segment 13 is disposed internal to segment 12 but still connected to delivery tube 30 via locking portion 54. In FIG. 2A, the distal end 14 can form the outer layer of the outer occlusive sack of segment 12 while the proximal end 16 can form the outer layer of the inner occlusive sack of segment 13.

Figure 2B:
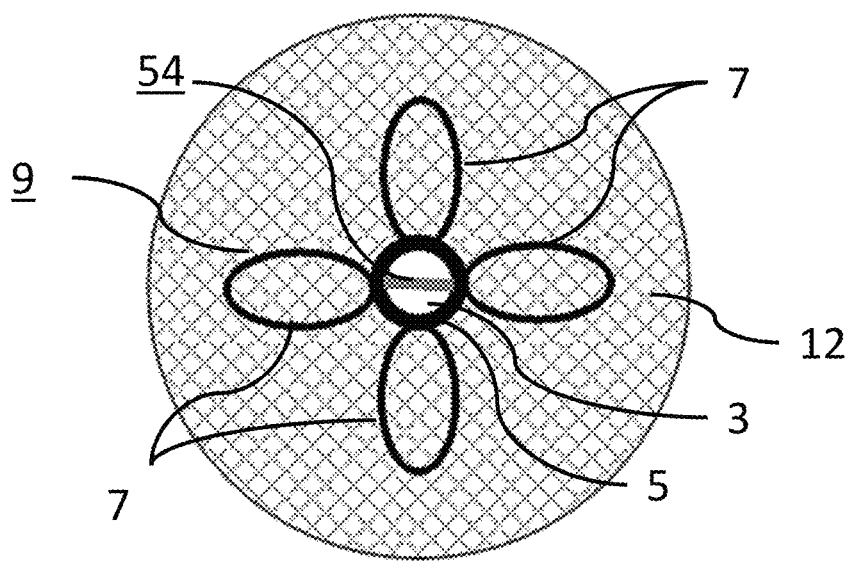
FIG. 2B is a schematic bottom view of an exemplary expansion mechanism and the outer occlusive sack of FIG. 2A with the delivery system removed.

FIG. 2B is a schematic bottom view of an exemplary expansion mechanism 9 and the outer occlusive sack of segment 12 in a deployed state and delivery system 40 removed for purposes of clarity only. As shown, flexible elements 7 of mechanism 9 can be radially spaced about a central axis of the expansion mechanism, including a central axis of expansion ring 5 and/or opening 3. The expansion mechanism 9 can include a plurality of expandable, flexible support elements 7 capable of urging portions on or adjacent end 16 of braid 10 from the collapsed state in microcatheter 20 to the deployed state distal of microcatheter 20. Each element 7 of mechanism 9 can include potential energy stored in the collapsed state (e.g. the support elements 7 may include biased bias elements or be memory shaped to expand a predetermined manner and release a predetermined amount of potential energy). The expandable support elements 7 of mechanism 9 can be configured to urge the proximal end of the first radially expandable segment from the collapsed to the deployed state by releasing the potential energy of the expandable support elements 7.

In certain embodiments, the expansion mechanism 9 can include at least four radially spaced flexible support elements 7 that extend from a central portion of mechanism 9, such as expansion ring 5. When collapsed, the expansion mechanism 9 can be sized to fit through the neck of the aneurysm. When expanded and delivered to the aneurysm, the expansion mechanism 9 can be larger and block the neck. As shown in FIG. 2B, one or more flexible support elements 7 of mechanism 9 can be a radially movable leaf that can move between collapsed to deployed conditions. However, mechanism 9 is not so limited and instead greater or fewer than four leaves, or other elongate flexible support elements 7 of different structure but similar function, can be included as needed or required. The expansion ring 5 and leaf or leaves of mechanism 9 can also be a monolithic structure formed from a memory alloy material such as nitinol. The central axis of the expansion mechanism 9 can be axially aligned with a central axis of segments 12 and/or 13. Locking portion 54 may also be attached to mechanism 9 and/or aligned therewith.

As shown in FIG. 1B and FIG. 2B, end 16 can be disposed on or adjacent mechanism 9, marker band 44, and/or locking portion 54. To form or assemble braid 10 as shown in FIGS. 1A-2B, end 14 and/or 18 of braid 10 can be inserted through the opening 3 of mechanism 9 and then the proximal end 16 of braid 10 can be folded over the opening 3. In certain embodiments, the end 14 and/or 18 can also be inserted through marker band 44 until proximal end 16 is disposed on or adjacent to band 44 at locking portion 54. Locking portion 54 can then be connected to and/or folded over end 16. Braid 10 is not so limited and instead of being folded over, proximal end 16 can be operatively connected to mechanism 9, locking portion 54, or any other component thereof by sonic weld, mechanical attachment, or adhesive. Regardless of connection, the proximal end 16 being operatively connected to mechanism 7, locking portion 54, and/or band 44, can cause formation of an outer layer of the braid 10 associated with segment 12.

In practice, as shown in FIGS. 3A to 4B, the braid 10 can be pushed into the aneurysm A by the delivery tube 30 and be deployed with the lower porosity outer layer of segment 12 laying across the neck of the aneurysm A, and the inner layer of segment 13 can be expanding inside of the outer layer while pushing the outer layer in position against the aneurysm wall and/or aneurysm neck. In particular, FIGS. 3A to 4B depict an enlarged schematic side view of the delivery system 40 and braid 10 as the braid 10 is being pushed into an example aneurysm A. Prior to the arrangement of FIG. 3A, the braid 10 can be assembled with a delivery tube 30 and/or a microcatheter 20 in a collapsed state and thus disposed inside delivery system 40. In this respect, the delivery system 40 and braid 10 can be packaged as a portable kit or system. The assembly between microcatheter 20, delivery tube 30, and/or braid 10 can take place before being introduced into the vasculature. The delivery system 40 used with braid 10, which can include microcatheter 20 and delivery tube 30, can be selectively positioned at the lesion site and delivery tube 30 can begin distally translating braid 10 towards the aneurysm.

Figure 3A:
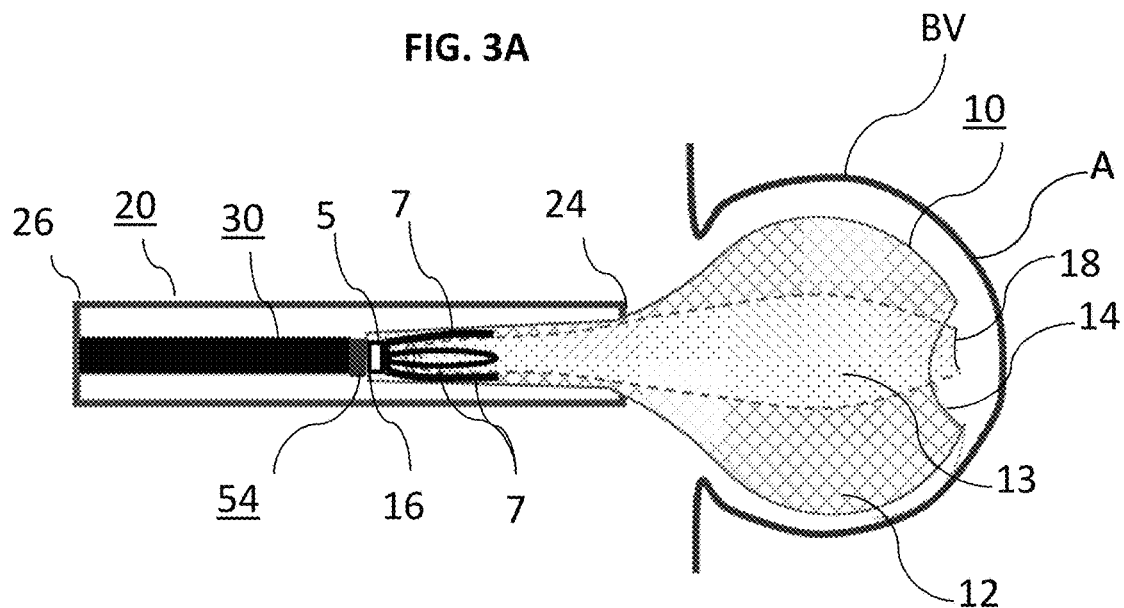
FIG. 3A is an enlarged schematic side view of the delivery system and braid of FIGS. 1-2 as the occlusive device is being pushed into an example aneurysm.

Turning to FIG. 3A, sack 12 has radially expanded towards the outer walls of aneurysm A while unexpanded portions (e.g. segment 13, end 16) of braid 10 continue to be mostly collapsed within microcatheter 20 and translated by delivery tube 30. Portions of braid 10 distal of end 24 can expand as braid 10 distally moves away from end 24 of catheter 20. When expanding from the collapsed state of FIG. 1B to the intermediary deployed state of FIG. 3A, segments 12 and 13 begin to radially expand to form their respective occlusive sacks within aneurysm A. Mechanism 9 is also depicted in FIG. 3A in a collapsed state completely contained within microcatheter 20. Ring 5 of mechanism 9 is shown in communication with end 16 while portions of elements 7 extend about segment 13 and in communication with segment 12 on or about end 16. In this respect, as braid 10 distally translates, segment 12 and/or segment 13 can be urged by elements 7 of mechanism 9 to form the occlusive sacks of this disclosure.

As shown in the transitional state of FIG. 3A, the sack of segment 12 can be generally spherical shape internal to aneurysm A while segment 13 remains mostly collapsed and stored within microcatheter 20. However, the portion of segment 13 distal of end 24 begun to radially expand within segment 12.

Figure 3B:
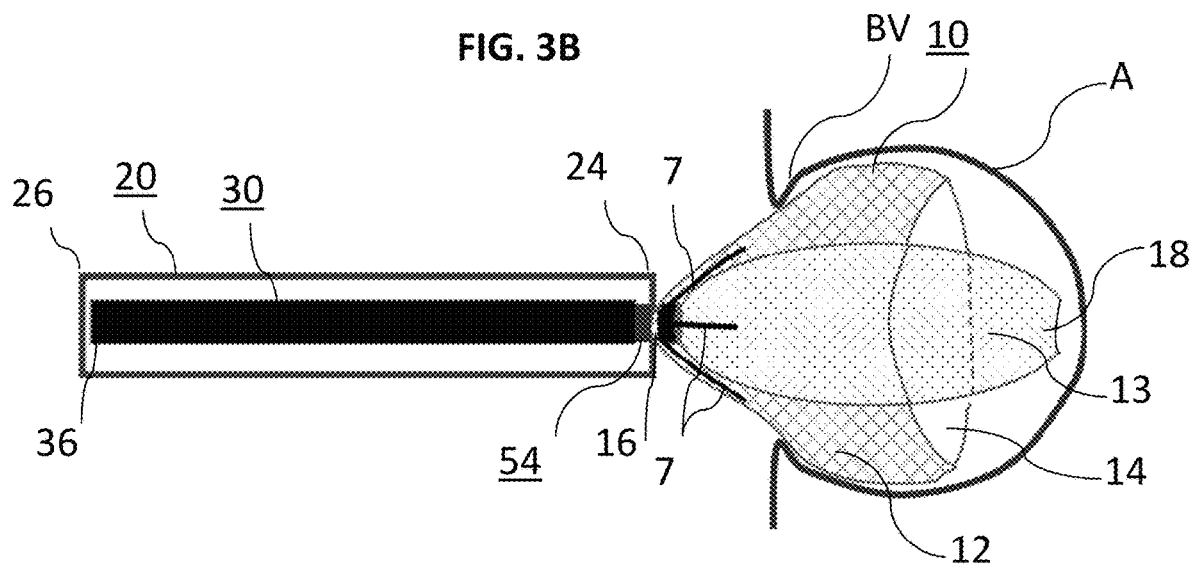
FIG. 3B is an enlarged schematic side view of the delivery system and braid of FIGS. 1-2 as the occlusive device is being pushed into an example aneurysm.

In FIG. 3B, the delivery tube 30 has distally slid braid 10 deeper into aneurysm A so that the outer surface of segment 12 has moved closer to contacting dome D. Locking portion 54 is depicted proximate or adjacent end 24 of microcatheter 20 so that all portions of braid 10, including mechanism 9, are distal thereof and external of microcatheter 20. As a result, elements 7 of mechanism 9 are shown urging expansion of segment 12 on or about end 16 to radially expand and form the outer occlusive sack shown filing the aneurysm A. It is understood that the outer surface of braid 10 can be made from nitinol with interwoven platinum filaments for radiopacity. Delivery tube 30 may be driven between FIGS. 3A and 3B by a hypotube from its proximal end 36 by an operator or the like. Microcatheter 20 may remain relatively stationary or fixed while delivery tube 30 can be seen distally translating braid 10 towards and through the neck of aneurysm A.

Braid 10 can include a pre-weakened or transition portion 19 (e.g., depicted in FIGS. 1A-1B) so that as braid 10 and delivery tube 30 are distally translated away from microcatheter 20 and deeper into aneurysm A, elements 7 of mechanism can urge segments 12 to expand and portion 19 can facilitate initiation of the radial expansion of segment 13 inside segment 12. For example, translation of braid 10 a first predetermined distance can cause segment 12 to radially expand to form its outer occlusive sack. Further translating braid a second predetermined distance into aneurysm A, as is shown in FIG. 3B can cause the inner occlusive sack of segment 13 to form inside of the outer occlusive sack. In certain embodiments, portion 19 can initiate radial expansion of segment 13 inside segment 12.

Figure 4A:
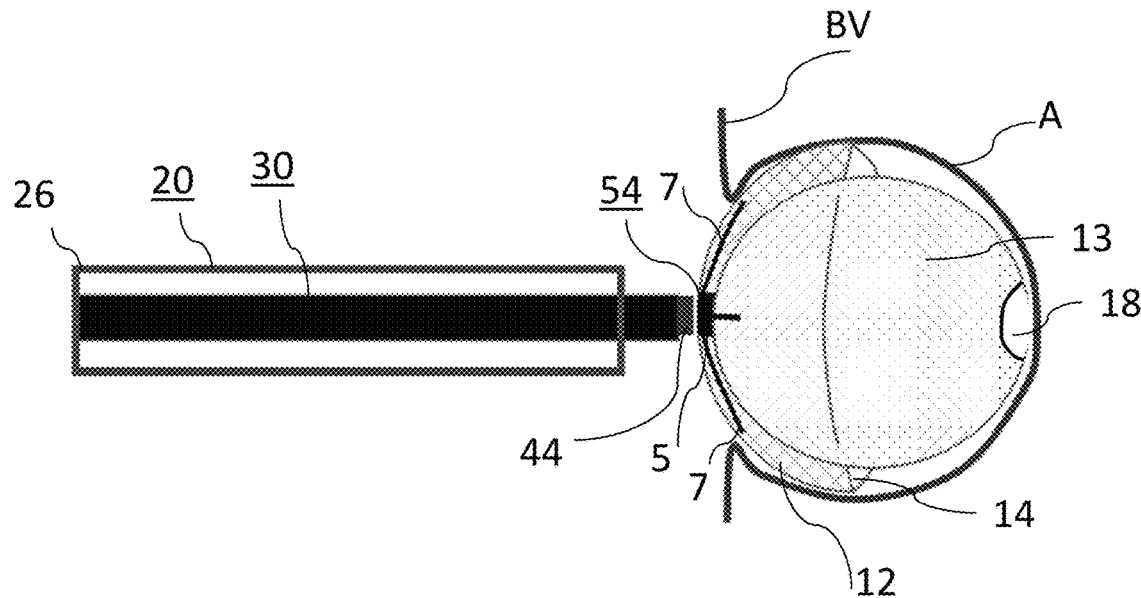
FIG. 4A is an enlarged schematic side view of the delivery system and braid of FIGS. 1-2 as the occlusive device is being pushed into an example aneurysm.

In FIG. 4A, the delivery tube 30 is distally translated deeper into aneurysm A. Moving between FIGS. 3A to 4A, it is shown that distally translating the braid 10, by the delivery tube 30, deeper into aneurysm A can further cause elements 7 of mechanism 9 to expand more and urge segment 12 to also additionally radially expand and press against the aneurysm wall. Further distal translation also can essentially cause locking portion 54 to make greater the expansion angle of segment 7 and push ring 5 of mechanism 9 towards the aneurysm neck. In turn, mechanism 9 is essentially tucked into braid segment 13 thereby flattening or otherwise rendering more spherical the sack of segment 12. In certain embodiments, the widening of segment 12 between FIGS. 3A and 4A can cause end 14 to slide proximally back towards end 24 of microcatheter while segment 13 continues to expand radially.

As also seen moving between FIGS. 3A to 4A, the junction between end 16 of braid 10, locking portion 54, mechanism 9, and delivery tube 30 can move from within microcatheter 20 in the collapsed state to completely within aneurysm A in the deployed state. Once braid 10, including segments 12 and 13, are selectively positioned and arranged to the desired condition (e.g. braid 10 has been translated distally to expand segments 12, 13 to form the outer and inner sacks), braid 10 can be detached from the delivery tube 30 as shown in FIG. 4B. In other words, as the braid 10 is distally translated towards the dome of the aneurysm A, segments 12, 13 can expand and be used to radially expand to support the aneurysm wall in a manner that is easy, efficient, and avoids risks of rupture.

Figure 4B:
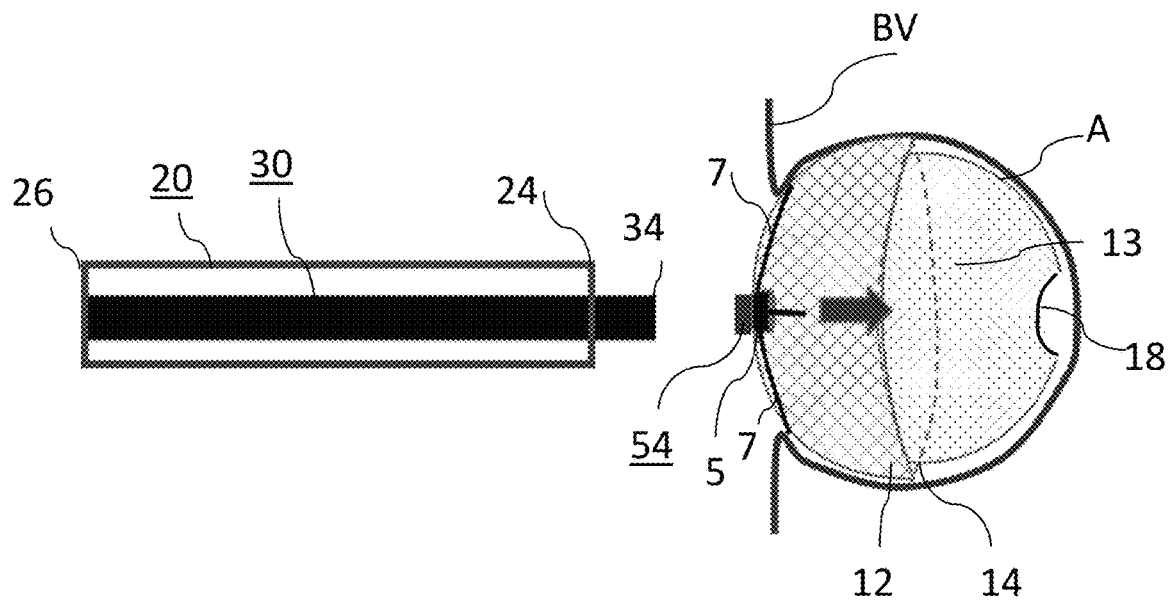
FIG. 4B is an enlarged schematic side view of the delivery system and braid of FIGS. 1-2 after the occlusive device is deployed into an example aneurysm.

Once expanded and positioned, delivery tube 30 can be proximally translated back into microcatheter 20 and retracted from the braid 10 and aneurysm A. In particular, FIG. 4B shows an example arrangement of braid 10 in its expanded state and the inner and outer sacks of segments 13 and 12, respectively, completely formed with delivery tube 30 having detached from locking portion 54. Expanding segments 12, 13 and positioning mechanism 9 into the braid 10 is particularly advantageous as it can prevent braid 10 from creating a protrusion that would otherwise extend into the parent vessel. Instead, any such protrusion can now be tucked into segment 12 and/or 13 of braid 10. Arranging braid 10 in this manner across the neck of the aneurysm while also varying the porosity of segments 12, 13 can also create a flow diversion essentially inside of the sacks of braid 10. FIG. 4B merely shows example spherical sacks of segments 12, 13 fully formed in a manner sufficient to occlude aneurysm. However, if either sack of segments 12, 13 is not precisely positioned or needs to be reset or adjusted within aneurysm A for safe occlusion without risk of rupture, braid 10 can be retracted back into microcatheter 20 by proximally withdrawing delivery tube 30 while still attached to braid 10.

Figure 5A:
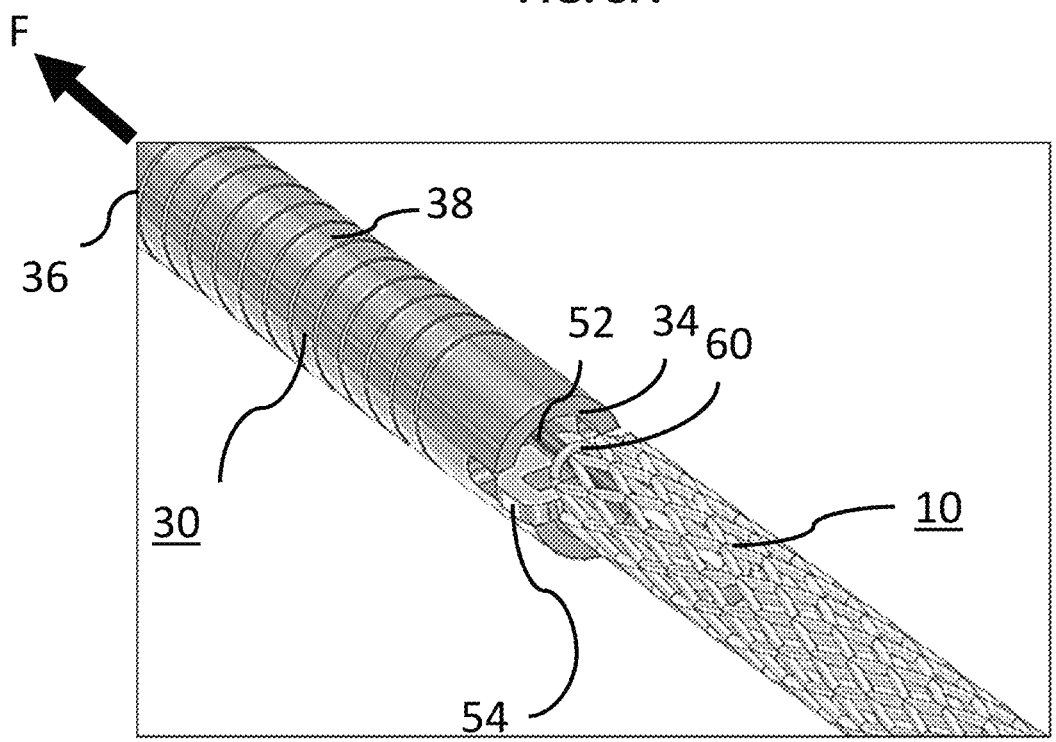
FIG. 5A is a perspective schematic view showing an exemplary delivery system for use with an example occlusive device.

FIGS. 5A to 6B generally illustrate example attachment and delivery between delivery tube 30 and braid 10 for deploying and detaching braid 10 in aneurysm A. The embodiments of FIGS. 5A to 6B is merely one way that delivery tube 30 and braid 10 may be attached at end 34 and any number of attachment means are contemplated as needed or required. The delivery tube 30 as shown can have a lumen extending from a proximal end 36 to a distal, delivery end 34. FIG. 5A illustrates braid 10 engaged with the locking member 52 and loop wire 58 locked into the locking portion 54. The opening 60 of the loop wire 58 can be placed through the locking portion 54. The locking portion 54 preferably takes the form of a small diameter elongate filament, however, other forms such as wires or tubular structures are also suitable. While the locking portion 54 is preferably formed of nitinol, other metals and materials such as stainless steel, PTFE, nylon, ceramic or glass fiber and composites may also be suitable. Locking member 52, in one example, may be an elongated retractable fiber that may extend between ends 24 and 26 of the microcatheter 20. Locking member 52 preferably takes the form of a small diameter elongate filament, however, other forms such as wires or tubular structures are also suitable. While the locking member 52 is preferably formed of nitinol, other metals and materials such as stainless steel, PTFE, nylon, ceramic or glass fiber and composites may also be suitable. When the locking member 52 is put through the opening 60 the braid 10 is now secure. It is understood that delivery tube 30 may include a compressible portion 38 disposed between its ends 34 and 36.

The compressible portion 38 can allow the delivery tube 30 to bend and/or flex. Such flexibility can assist tracking the braid 10 through the microcatheter 20 and the tortuous path through the vasculature. The compressible portion 38 can be formed with interference spiral cuts that can allow for gaps to permit bending but in one example, do not act as a spiral-cut spring. Compressible portion 38 can be axially adjustable between an elongated condition and a compressed condition. However, any other arrangement allowing axial adjustment (e.g., a wound wire or spiral ribbon) can also be suitable for use with detachment systems according to the present disclosure). The compressible portion 38 can be in the elongated condition at rest and automatically or resiliently returns to the elongated condition from a compressed condition, unless otherwise constrained. The function of the compressible portion 38 is described in greater detail herein.

Figure 5B:
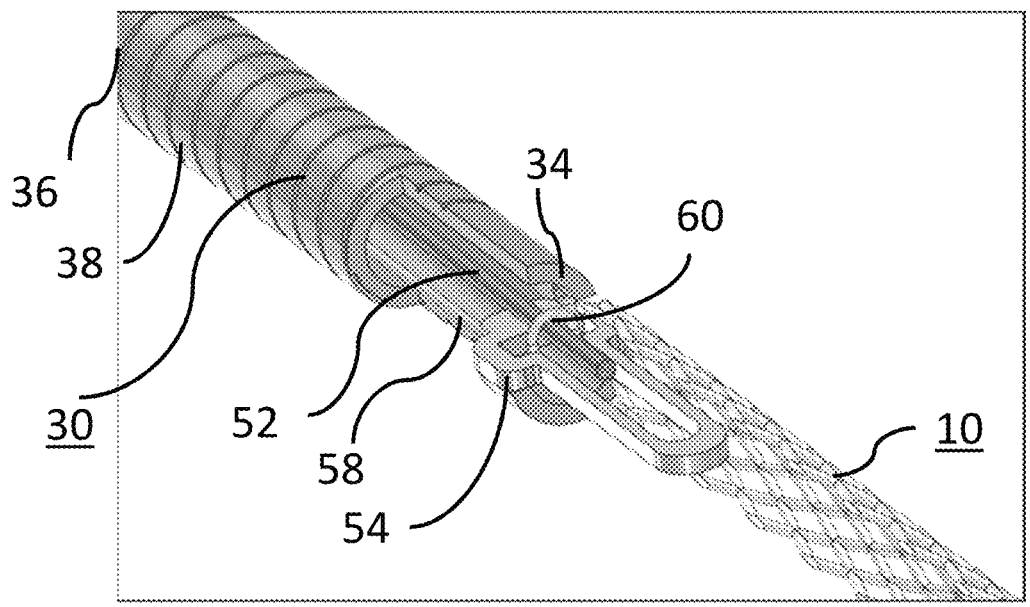
FIG. 5B is a perspective schematic view of FIG. 5A but with partial cross-section of the delivery system and the occlusive device.
Figure 6A:
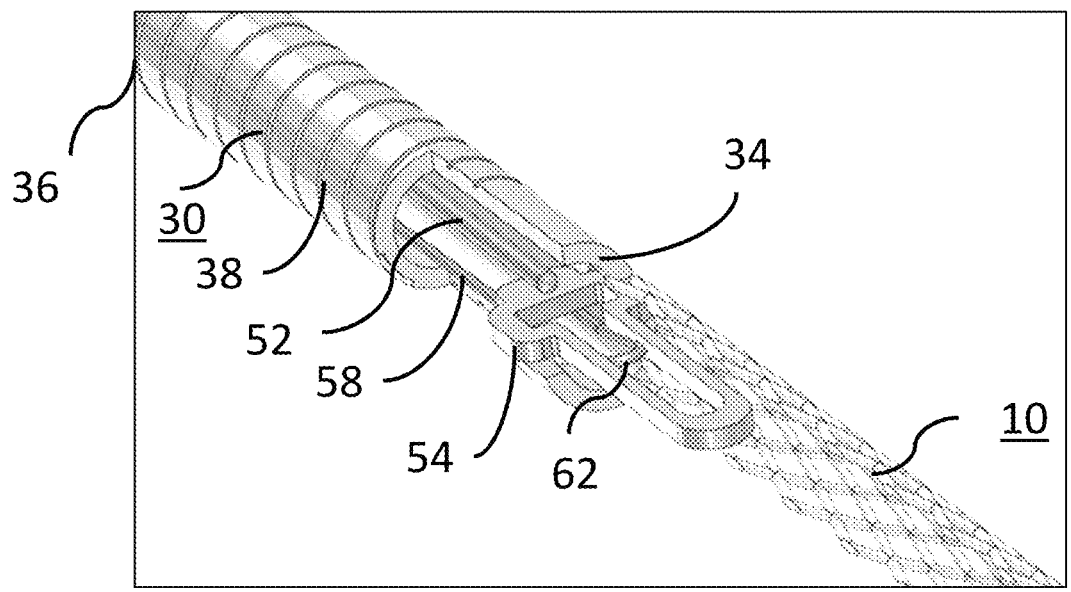
FIG. 6A is a perspective schematic view of FIGS. 5A-5B being deployed with partial cross-section of the delivery system and the occlusive device.
Figure 6B:
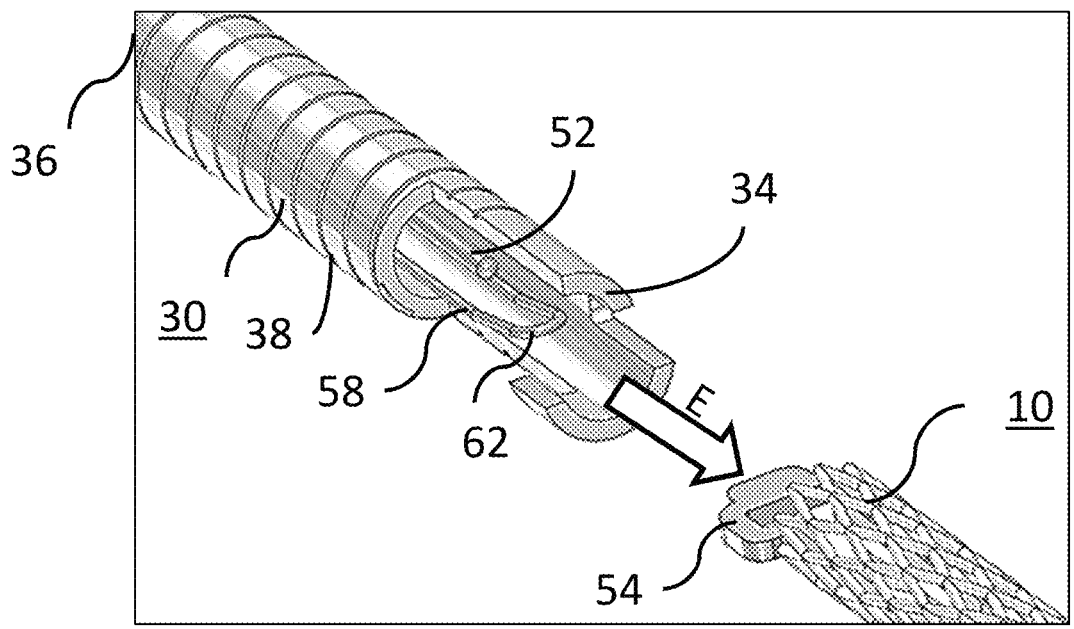
FIG. 6B is a perspective schematic view of FIGS. 5A-5B deployed with the exemplary delivery system detached from the occlusive device.

A force F was previously applied to place the delivery tube 30 in a compressed state. FIG. 5B illustrates the locking member 52 being drawn proximally to begin the release sequence for braid 10. FIG. 6A illustrates the instant the locking member 52 exits the opening 60 and is pulled free of the loop wire 58. The distal end 62 of the loop wire 58 falls away/returns to its preformed shape and exits the locking portion 54. As can be seen, there is now nothing holding the braid 10 to the delivery tube 30. FIG. 6B illustrates the end of the release sequence. Here, the compressible portion 38 of the delivery tube 30 has expanded/returned to its original shape and "sprung" forward. An elastic force E is imparted by the distal end 34 of the delivery tube 30 to the braid 10 to "push" it away to insure a clean separation and delivery of the braid 10 to the aneurysm A. It is to be understood that the delivery scheme described in FIGS. 6A-7B are merely example approaches to delivery of braid 10.

Figure 7:
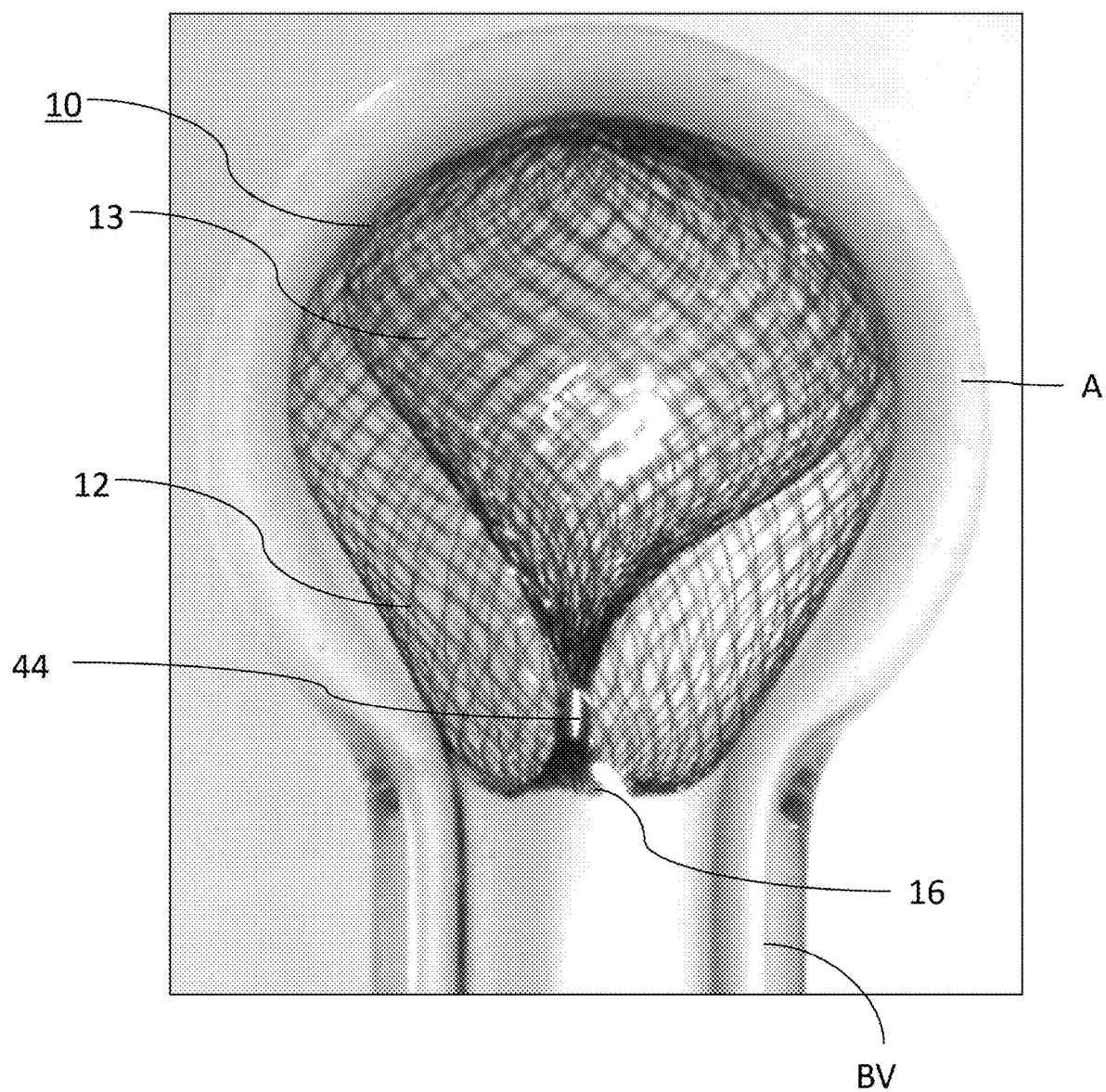
FIG. 7 depicts an example braid of this disclosure deployed in an example aneurysm.
Figure 8A:
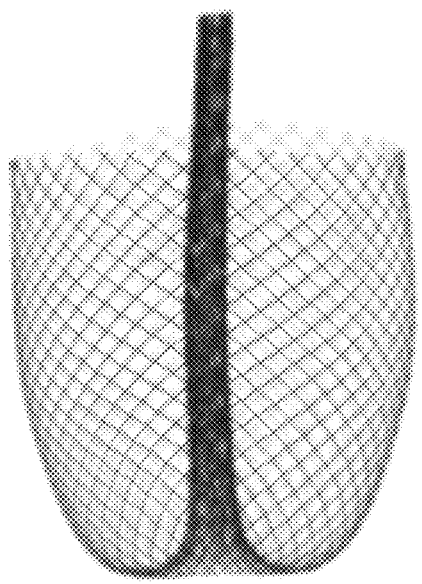
FIG. 8A depicts an example prototype braid of this disclosure without an example expansion mechanism.
Figure 8B:
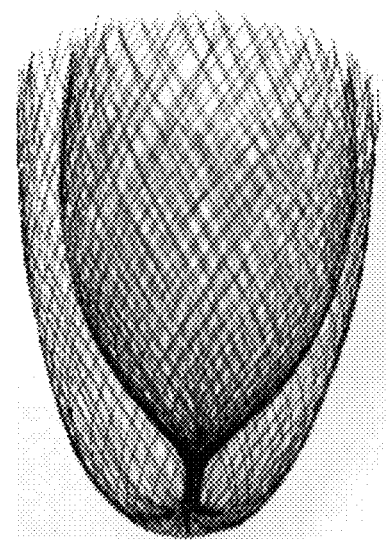
FIG. 8B depicts an example prototype braid of this disclosure without an example expansion mechanism.
Figure 8C:
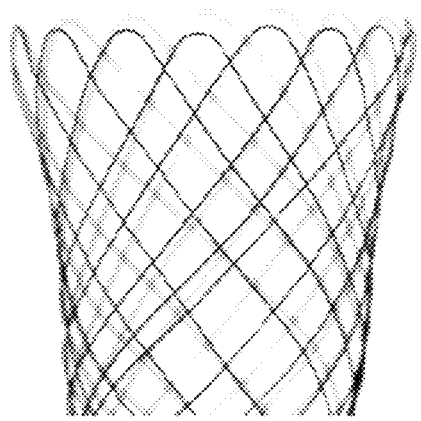
FIG. 8C depicts an example prototype braid of this disclosure without an example expansion mechanism.
Figure 8D:
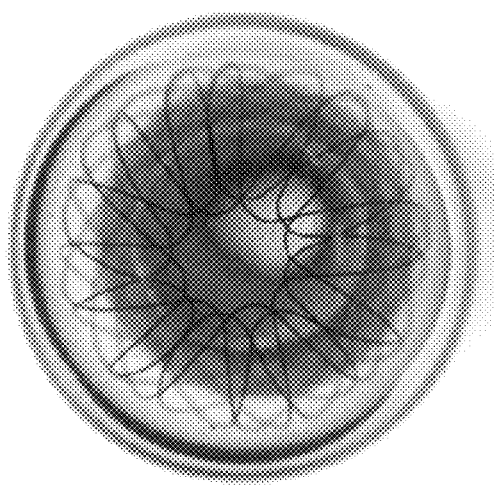
FIG. 8D depicts an example prototype braid of this disclosure without an example expansion mechanism.

FIG. 7 depicts an example braid 10 of this disclosure deployed in an example aneurysm A.

FIGS. 8A-8D depict example prototype braids of this disclosure with varying braid properties. These prototypes are strictly for illustrative purposes.

FIG. 9 is a flow diagram for a method 900 of delivering an occlusive device to the aneurysm. Step 905 includes positioning a radially expandable braid within a microcatheter, the braid being in a collapsed state within the microcatheter and comprising a distal end and a proximal end. Step 910 includes attaching the proximal end of the braid to the distal end of a delivery tube. Step 915 includes distally sliding the braid from the microcatheter, by the delivery tube, towards an aneurysm. Step 920 includes urging a first radially expandable segment of the braid to form an outer occlusive sack by expanding an expansion mechanism of the braid expands, the expansion mechanism attached to the proximal end of the braid, the outer occlusive sack being operable to lay across a neck of the aneurysm. Step 925 further distally pushing the braid thereby expanding a second radially expandable segment inside of the outer occlusive sack while distally pushing the outer occlusive sack against the aneurysm wall and the neck of the aneurysm. Step 930 releasing the braid, including the outer and inner occlusive sacks, and withdrawing the delivery tube and the microcatheter from the aneurysm. The outer occlusive sack can form upon or as the distal end of the braid is moved distally from the microcatheter and in communication with a dome of the aneurysm.

In certain embodiments of method 900, the expansion mechanism can include a plurality of radially spaced flexible elements, each flexible element capable of expanding from a collapsed condition in the microcatheter to an expanded condition in the deployed state to support a proximal portion of the outer occlusive sack. In this respect, the method 900 can also include axially aligning the central axis of the expansion mechanism with a central axis of the first and second radially expandable segments; and radially spacing each flexible element about the central axis of the expansion mechanism.

The method 900 can also include providing an expansion ring with an opening on or with the expansion mechanism; inserting a distal end of the braid through the opening; and folding the proximal end of the braid over the opening. The method 900 can also include radially spacing, about the expansion mechanism, at least four flexible elements that extend from an expansion ring, each flexible element being a radially movable leaf capable of moving between collapsed to deployed conditions. The method 900 can also include forming a monolithic structure from the expansion ring and the at least four flexible elements. The method 900 can also include forming a plurality of expandable support elements on the expansion mechanism that comprise potential energy stored in the collapsed state; and urging, by the expandable support elements, the proximal end of the first radially expandable segment from the collapsed to the deployed state by releasing the potential energy. The method 900 can also include forming the first radially expandable segment with a porosity lower than a porosity of the second radially expandable segment; positioning the first radially expandable segment adjacent or in communication with a neck of the aneurysm; and inducing a flow diverting effect across the neck of the aneurysm when the inner occlusive sack is formed inside the outer occlusive sack.

It is understood that variations of the braid 10 can include various materials such as stainless steel, bio absorbable materials, and polymers. Braid 10, including any specific portions such as any breaks, varying regions of differing porosities, and occlusive sacks, can be heat set to various configurations such as spherical, oblong, saddle shaped, or the like, for the purpose of shaping the outer and/or inner sack to better match the aneurysm morphology. In addition, the braid 10 can be heat shaped to include weak points to facility the radial expansion of the occlusive sacks. Further, interstices of braid 10 that form the sacks can vary, or be selectively designed, in size or shape along its length depending on how much braid 10 is caused to radially expand as delivery tube 30 is distally moved.

It is understood that the braid 10 can also be included in a system or otherwise in communication with an imaging device capable of imaging the outer and/or inner occlusive sacks of segments 12 and 13 with respect to the aneurysm. An orientation of the outer and/or inner occlusive sacks can be adjustable by the braid 10 being distally or proximally moved with respect to the aneurysm and monitored precisely by the imaging device.

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

What is claimed is:

1. A braid for treating an aneurysm, the braid comprising:
a first radially expandable segment operable to move from a collapsed state within a microcatheter to a deployed state distal of the microcatheter, wherein the first radially expandable segment is capable of radially expanding to form an outer occlusive sack in the aneurysm that seals the neck of the aneurysm in the deployed state;
a second radially expandable segment operable to move from the collapsed state within the microcatheter to the deployed state distal of the microcatheter, wherein the second radially expandable segment is capable of radially expanding inside the outer occlusive sack to form an inner occlusive sack in the outer occlusive sack in the deployed state;
the braid configured so that distally translating the braid in the aneurysm as the outer occlusive sack is forming causes an inner layer of the braid inside of the outer occlusive sack to radially independently expand inside the outer occlusive sack and form the inner occlusive sack;
proximal ends of each segment aligned with each other in both the collapsed and deployed states and the distal ends of each segment being positioned on equivalent sides opposite the proximal ends of each segment in both the collapsed and deployed states; and
an expansion mechanism disposed comprising an opening and a plurality of radially flexible elements surrounding the opening, each flexible element capable of expanding from a collapsed condition in the microcatheter to an expanded condition in the deployed state to support a proximal portion of the outer occlusive segment, the expansion mechanism being positioned at a proximal end of the first and second radially expandable segments.

2. The braid of claim 1, a distal end of the braid being insertable through the opening and the proximal end being folded over the opening.

3. The braid of claim 1, wherein each radially flexible element is evenly radially spaced about a central axis of the expansion mechanism, the central axis of the expansion mechanism being axially aligned with a central axis of the first and second radially expandable segments.

4. The braid of claim 1, wherein the expansion mechanism comprises at least four radially spaced flexible elements that extend from an expansion ring, each flexible element being a radially movable leaf capable of moving between collapsed to deployed conditions.

5. The braid of claim 4, wherein the expansion ring and leaves are formed from a memory alloy material.

6. The braid of claim 1, wherein the expansion mechanism comprises a plurality of expandable support elements that comprise potential energy stored in the collapsed state, wherein the expandable support elements are configured to urge the proximal end of the first radially expandable segment from the collapsed to the deployed state by releasing the potential energy of the expandable support elements.

7. The braid of claim 1, wherein a porosity of the inner occlusive sack is greater than a porosity of the outer occlusive sack.

8. The braid of claim 1, wherein the inner layer of the braid is capable of radially expanding inside the outer occlusive sack while the outer occlusive sack is pushed against the aneurysm wall and aneurysm neck.

9. The braid of claim 1, further comprising a marker band in communication with the proximal end of the braid,
wherein the inner layer that radially expands inside the outer occlusive sack is formed by folding the proximal end over the marker band.

10. The braid of claim 1, wherein in the deployed state, the braid is detachable from a delivery system in the aneurysm, the delivery system comprising:
a microcatheter; and
a delivery tube comprising a distal end and a proximal end, the distal end of the delivery tube being detachably connected to the proximal end of the braid, the delivery tube being translatably disposable within the microcatheter;
wherein the delivery tube is capable of distally translating the braid within the microcatheter from the collapsed state to the deployed state.

11. The braid of claim 1, wherein dimensions of interstices of the braid vary at the proximal end versus the distal end so that a porosity of the outer occlusive sack is less than a porosity of the inner occlusive sack.

12. An occlusive device for treating an aneurysm, comprising:
a braid being translatably disposable within a microcatheter from a collapsed state to a deployed state, the braid comprising a distal end and a proximal end;
wherein in the deployed state, the braid comprises:
an outer occlusive mesh sack comprising a proximal end and a distal end and capable of pushing against an aneurysm wall of the aneurysm and sealing a neck of the aneurysm to at least one of deflect, divert, and slow a flow into the aneurysm;
an inner occlusive mesh sack comprising a proximal end and a distal end and disposed inside the outer occlusive sack;
the braid configured so that distally translating the braid in the aneurysm as the outer occlusive sack is forming causes an inner layer of the braid inside of the outer occlusive sack to radially expand inside the outer occlusive sack and form the inner occlusive sack;
proximal ends of each sack aligned with each other in both the collapsed and deployed states and the distal ends of each sack being positioned on equivalent sides opposite the proximal ends of each sack in both the collapsed and deployed states; and
an expansion mechanism disposed at the proximal end urging formation of at least one of the outer and inner occlusive sacks in the deployed state, the expansion mechanism comprising a plurality of radially spaced flexible elements to form a radially movable leaf capable of moving between collapsed to deployed conditions.

13. A method of occluding an aneurysm, comprising:
positioning a radially expandable braid within a microcatheter, the braid being in a collapsed state within the microcatheter and comprising a distal end and a proximal end;
attaching the proximal end of the braid to the distal end of a delivery tube;
distally sliding the braid from the microcatheter, by the delivery tube, towards the aneurysm;
urging a first radially expandable mesh segment of the braid to form an outer occlusive sack by expanding an expansion mechanism of the braid, the first radially expandable mesh segment comprising a proximal end and a distal end, wherein the expansion mechanism is attached to the proximal end of the braid;
laying the outer occlusive sack across a neck of the aneurysm; and
further distally pushing the braid in the aneurysm as the outer occlusive sack is forming thereby expanding a second radially expandable mesh segment inside of the outer occlusive sack to form an inner occlusive sack while distally pushing the outer occlusive sack against the aneurysm wall and the neck of the aneurysm, the second radially expandable mesh segment comprising a proximal end and a distal end;
the proximal ends of each segment aligned with each other in both the collapsed and deployed states and the distal ends of each segment being positioned on equivalent sides opposite the proximal ends of each segment in both the collapsed and deployed states.

14. The method of claim 13, wherein the expansion mechanism comprises a plurality of radially spaced flexible elements, each flexible element capable of expanding from a collapsed condition in the microcatheter to an expanded condition in the deployed state to support a proximal portion of the outer occlusive sack, the method further comprising:
axially aligning the central axis of the expansion mechanism with a central axis of the first and second radially expandable segments; and
radially spacing each flexible element about the central axis of the expansion mechanism.

15. The method of claim 13, the method further comprising:
providing an expansion ring with an opening on or with the expansion mechanism;
inserting a distal end of the braid through the opening; and
folding the proximal end of the braid over the opening.

16. The method of claim 13, further comprising:
radially spacing, about the expansion mechanism, at least four flexible elements that extend from an expansion ring, each flexible element being a radially movable leaf capable of moving between collapsed to deployed conditions.

17. The method of claim 13, further comprising:
forming a plurality of expandable support elements on the expansion mechanism that comprise potential energy stored in the collapsed state; and
urging, by the expandable support elements, the proximal end of the first radially expandable segment from the collapsed to the deployed state by releasing the potential energy.

18. The method of claim 13, further comprising:
forming the first radially expandable segment with a porosity lower than a porosity of the second radially expandable segment;
positioning the first radially expandable segment adjacent or in communication with a neck of the aneurysm; and
at least one of deflecting, diverting, and slowing a flow into the aneurysm.

* * * * *